United States Patent
Ingle

(10) Patent No.: US 10,462,412 B2
(45) Date of Patent: Oct. 29, 2019

(54) SURGICAL VISUALIZATION AND RECORDING SYSTEM

(71) Applicant: Manish Eknath Ingle, North Wales, PA (US)

(72) Inventor: Manish Eknath Ingle, North Wales, PA (US)

( * ) Notice: Subject to any disclaimer, the term of this patent is extended or adjusted under 35 U.S.C. 154(b) by 24 days.

(21) Appl. No.: 15/884,359

(22) Filed: Jan. 30, 2018

(65) Prior Publication Data

US 2019/0238791 A1    Aug. 1, 2019

(51) Int. Cl.

| H04N 7/015 | (2006.01) |
|---|---|
| H04N 5/232 | (2006.01) |
| H04N 5/76 | (2006.01) |
| H04N 5/272 | (2006.01) |
| A61B 1/04 | (2006.01) |
| A61B 1/00 | (2006.01) |
| A61B 90/00 | (2016.01) |
| A61B 1/313 | (2006.01) |
| H04N 5/225 | (2006.01) |

(52) U.S. Cl.
CPC ......... H04N 7/015 (2013.01); A61B 1/00016 (2013.01); A61B 1/00043 (2013.01); A61B 1/04 (2013.01); A61B 1/3132 (2013.01); A61B 90/361 (2016.02); A61B 90/37 (2016.02); H04N 5/23216 (2013.01); H04N 5/23293 (2013.01); H04N 5/272 (2013.01); H04N 5/76 (2013.01); A61B 2090/373 (2016.02); H04N 2005/2255 (2013.01)

(58) Field of Classification Search
CPC .... H04N 7/015; H04N 5/23293; H04N 5/272; H04N 5/76; H04N 5/23216; H04N 2005/2255; A61B 90/37; A61B 90/361; A61B 2090/373; A61B 1/3132; A61B 1/00016; A61B 1/00043; A61B 1/04
USPC ......................................................... 348/74
See application file for complete search history.

(56) References Cited

U.S. PATENT DOCUMENTS

| 5,877,819 A | 3/1999 | Branson |
|---|---|---|
| 8,858,425 B2 | 10/2014 | Farr et al. |
| 9,706,903 B2 | 7/2017 | Kirma et al. |

(Continued)

FOREIGN PATENT DOCUMENTS

| CN | 106791675 A | 5/2017 |
|---|---|---|
| JP | 2017158764 A | 9/2017 |

*Primary Examiner* — Allen C Wong
(74) *Attorney, Agent, or Firm* — Ashok Tankha

(57) ABSTRACT

A method and a surgical visualization and recording system (SVRS) for capturing, communicating, and displaying images of a surgical site with up to a 4K ultrahigh definition (UHD) resolution in association with patient information in real time during a surgery are provided. The SVRS includes a UHD camera system with an optical component and an image sensor, and a display unit with an embedded microcomputer and a tactile user interface (TUI). The image sensor captures and communicates images of the surgical site with up to a 4K UHD resolution to the embedded microcomputer. The embedded microcomputer receives patient information via the TUI, and associates the captured and communicated images of the surgical site with the patient information in real time. The display unit displays the captured and communicated images of the surgical site with the patient information with up to a 4K UHD resolution on the TUI in real time.

23 Claims, 17 Drawing Sheets

(56) References Cited

U.S. PATENT DOCUMENTS

| | | | |
|---|---|---|---|
| 2015/0109402 A1* | 4/2015 | Tian | H04N 5/23296 348/14.07 |
| 2015/0254422 A1* | 9/2015 | Avisar | G09B 23/28 703/11 |
| 2018/0012074 A1* | 1/2018 | Holz | G06K 9/00671 |
| 2018/0058851 A1* | 3/2018 | Amling | G01C 11/04 |
| 2018/0082480 A1* | 3/2018 | White | A61B 50/33 |

* cited by examiner

SURGICAL VISUALIZATION AND RECORDING SYSTEM

BACKGROUND

Minimally invasive surgeries, for example, laparoscopy, arthroscopy, thoracoscopy, etc., are being increasingly performed for reducing trauma to a patient's tissues, lessening scarring, minimizing post-surgical pain, reducing blood loss, reducing a risk of infection, and allowing a quick recovery of the patient. During a minimally invasive surgery, a surgeon makes small incisions of, for example, a few millimeters through the skin of the patient instead of making one large opening in the patient's body as performed in conventional open surgery. A conventional surgical visualization system used during a minimally invasive surgery comprises a camera head, an external control unit, and a monitor for visualizing a surgical site. A surgeon passes an elongated thin tube with a camera attached at a proximal end of a scope device, for example, a laparoscope through one of the incisions, and passes other instruments that facilitate in performing the minimally invasive surgery, through the other incisions. The camera captures images, for example, still images, videos, etc., of the surgical site. The external control unit receives and processes image signals from the camera and projects an image, for example, a still image or a moving image such as a video of the surgical site onto the monitor in an operating room to provide the surgeon a clear and magnified view of the surgical site. The surgeon may use hardware controls of the external control unit for setting image parameters such as brightness, saturation, contrast, etc., related to the captured image and for controlling other aspects of the captured image.

The conventional surgical visualization system comprising the camera head, the external control unit, and the monitor is a bulky system of separate devices, typically spaced apart, for capturing and displaying images of a surgical site during a minimally invasive surgery. To modify the image parameters, a user, for example, the surgeon must locate the hardware controls such as buttons on the external control unit and operate the buttons continuously, while simultaneously visualizing the captured images in real time on the monitor. Modifying the image parameters of the captured images in real time during the minimally invasive surgery may distract the surgeon performing the minimally invasive surgery as the surgeon has to simultaneously manage different devices that are spaced apart. A real time review of the captured images is not supported by the conventional surgical visualization system. An external media viewer or an external computing device, for example, a laptop or a tablet computer, is typically connected to the conventional surgical visualization system to allow the surgeon to review the captured images of the surgical site. Moreover, conventional surgical visualization systems typically capture low resolution images that are difficult to view and interpret optimally. Furthermore, the conventional surgical visualization system requires a separate recording system for capturing and recording the images, which may result in mishandling and identification of patient information.

The surgeon who performs the minimally invasive surgery must have access to patient information comprising, for example, the patient's name, age, gender, a patient identifier, medical history, information on the minimally invasive surgery to be performed, etc., prior to, during, after, and at any instance of the minimally invasive surgery. Access to the patient information allows the surgeon to plan the minimally invasive surgery carefully and to react to the on-going surgical procedure, thereby increasing success of the minimally invasive surgery. In contrast, in conventional surgical visualization systems, for example, a hospital may maintain a handwritten document or an electronic document of the patient information, which needs to be transmitted to the surgeon for access prior to, during, after, and at any instance of the minimally invasive surgery. Handling the handwritten document containing the patient information and visualizing the images of the surgical site captured by the conventional surgical visualization system in real time during the minimally invasive surgery, or viewing the electronic document containing the patient information on an external media player, for example, on a laptop or a tablet computer, and visualizing the captured images of the surgical site in real time during the minimally invasive surgery, can be cumbersome and obstructive for the surgeon, thereby creating a less than optimal situation for performing the minimally invasive surgery.

The images of the surgical site captured by the conventional surgical visualization system are typically stored within the conventional surgical visualization system and can be reviewed using an external media viewer. Physical accessibility to the conventional surgical visualization system is required to allow the surgeon to review the captured images of the surgical site. A technical glitch in the conventional surgical visualization system can corrupt data stored in the conventional surgical visualization system or may provide access of the captured images to unauthorized individuals. Manual transfer of the captured images of the surgical site to another device poses a risk of mishandling and manipulation of the captured images.

Hence, there is a long felt need for a method and a surgical visualization and recording system comprising embedded image capture, recording, control, and display components for capturing, communicating, recording, and displaying images of a surgical site with up to a 4K ultrahigh definition (UHD) resolution of 3840 pixels×2160 lines in association with patient information in real time during a surgery, for example, a minimally invasive surgery. Moreover, there is a need for a method and a surgical visualization and recording system comprising an integrated visualization interface for accepting user inputs for modifying image parameters of the captured images of the surgical site without an external control unit, and for allowing a user, for example, a surgeon to review the captured images with up to a 4K UHD resolution along with the patient information without an external media viewer or an external computing device, for example, a laptop or a tablet computer, during and after the surgery. Furthermore, there is a need for a method and a surgical visualization and recording system for accepting user inputs for entering additional patient information in an integrated visualization interface and associating the patient information with the captured images in real time to reduce paperwork required to associate the captured images to a patient. Furthermore, there is a need for a method and a surgical visualization and recording system for allowing a user, for example, a surgeon to record 4K UHD resolution images directly to a storage device, for example, a flash drive, a hard drive, or a network drive on a secure hospital network to preclude unauthorized staff from handling the captured images along with the patient information and to maintain confidentiality of the patient information under the Health Insurance Portability and Accountability Act (HIPAA). Furthermore, there is a need for a method and a surgical visualization and recording system for automatically and securely transmitting the captured images of the surgical site for direct and secure storage on an external system and/or in a cloud computing environment over a network, for example, an internal hospital network in real time.

SUMMARY OF THE INVENTION

This summary is provided to introduce a selection of concepts in a simplified form that are further disclosed in the detailed description of the invention. This summary is not intended to determine the scope of the claimed subject matter.

The method and the surgical visualization and recording system (SVRS) comprising embedded image capture, recording, control, and display components disclosed herein address the above recited need for capturing, communicating, recording, and displaying images of a surgical site with up to an ultrahigh definition (UHD) resolution of 3840 pixels×2160 lines, hereafter referred as "4K UHD resolution", in a UHD format in association with patient information in real time during a surgery, for example, a minimally invasive surgery. The method and the SVRS disclosed herein provide an integrated visualization interface, that is, a tactile user interface, for accepting user inputs for modifying image parameters of the captured images of the surgical site without an external control unit, and for allowing a user, for example, a surgeon to review the captured images with up to a 4K UHD resolution along with the patient information without an external media viewer or an external computing device, for example, a laptop or a tablet computer, during and after the surgery. The tactile user interface of the SVRS disclosed herein also accepts user inputs for entering additional patient information. The SVRS associates the patient information with the captured images in real time, thereby reducing paperwork required to associate the captured images to a patient.

Furthermore, the method and the surgical visualization and recording system (SVRS) disclosed herein allow a user, for example, a surgeon to record 4K ultrahigh definition (UHD) resolution images directly to a storage device, for example, a flash drive, a hard drive, or a network drive on a secure hospital network, thereby precluding unauthorized staff from handling the captured images along with the patient information, and maintaining confidentiality of the patient information under the Health Insurance Portability and Accountability Act (HIPAA). Furthermore, the method and the SVRS disclosed herein address the above recited need for automatically and securely transmitting the captured images of the surgical site for direct and secure storage on an external system and/or in a cloud computing environment over a network, for example, an internal hospital network in real time. The SVRS eliminates the need for handling external media to transmit and load the captured images in a hospital network or on a hospital server. A hospital network drive can be mapped to the SVRS for storing the captured images during the initial setup of the SVRS.

In the method disclosed herein, the surgical visualization and recording system (SVRS) comprising an ultrahigh definition (UHD) camera system and a display unit is provided for capturing, communicating, and displaying images of a surgical site with up to a 4K UHD resolution in association with patient information in real time during a surgery. The UHD camera system comprises an optical component and an image sensor. The optical component and the image sensor are positioned at a proximal end of a surgical scope device, for example, a laparoscope. The image sensor is in optical communication with the optical component for receiving reflected light from the surgical site via the optical component and capturing images of the surgical site with up to a 4K UHD resolution. The display unit comprises an embedded microcomputer and the tactile user interface. The embedded microcomputer is in operable communication with the UHD camera system. The embedded microcomputer comprises at least one processor configured to execute computer program instructions for receiving, transforming, and processing the captured images of the surgical site. The tactile user interface is in operable communication with the embedded microcomputer for receiving one or more user inputs for controlling operation of the UHD camera system and for displaying the processed images of the surgical site with up to a 4K UHD resolution.

When a user, for example, a surgeon performing the surgery, enters patient information via the tactile user interface of the display unit, the embedded microcomputer of the display unit receives the patient information. The image sensor of the ultrahigh definition (UHD) camera system captures the images of the surgical site with up to a 4K UHD resolution and communicates the captured images to the embedded microcomputer of the display unit in real time, on receiving one or more user inputs via the tactile user interface of the display unit and/or via one or more input devices operably connected to the embedded microcomputer. The embedded microcomputer associates the captured and communicated images of the surgical site with the received patient information in real time. The display unit displays the captured and communicated images of the surgical site associated with the received patient information with up to a 4K UHD resolution on the tactile user interface in real time.

In one or more embodiments, related systems comprise circuitry and/or programming for effecting the methods disclosed herein. The circuitry and/or programming can be any combination of hardware, software, and/or firmware configured to affect the methods disclosed herein depending upon the design choices of a system designer. Also, in an embodiment, various structural elements can be employed depending on the design choices of the system designer.

BRIEF DESCRIPTION OF THE DRAWINGS

The foregoing summary, as well as the following detailed description of the invention, is better understood when read in conjunction with the appended drawings. For illustrating the invention, exemplary constructions of the invention are shown in the drawings. However, the invention is not limited to the specific methods and components disclosed herein. The description of a method step or a component referenced by a numeral in a drawing is applicable to the description of that method step or component shown by that same numeral in any subsequent drawing herein.

DETAILED DESCRIPTION OF THE INVENTION

Figure 1:
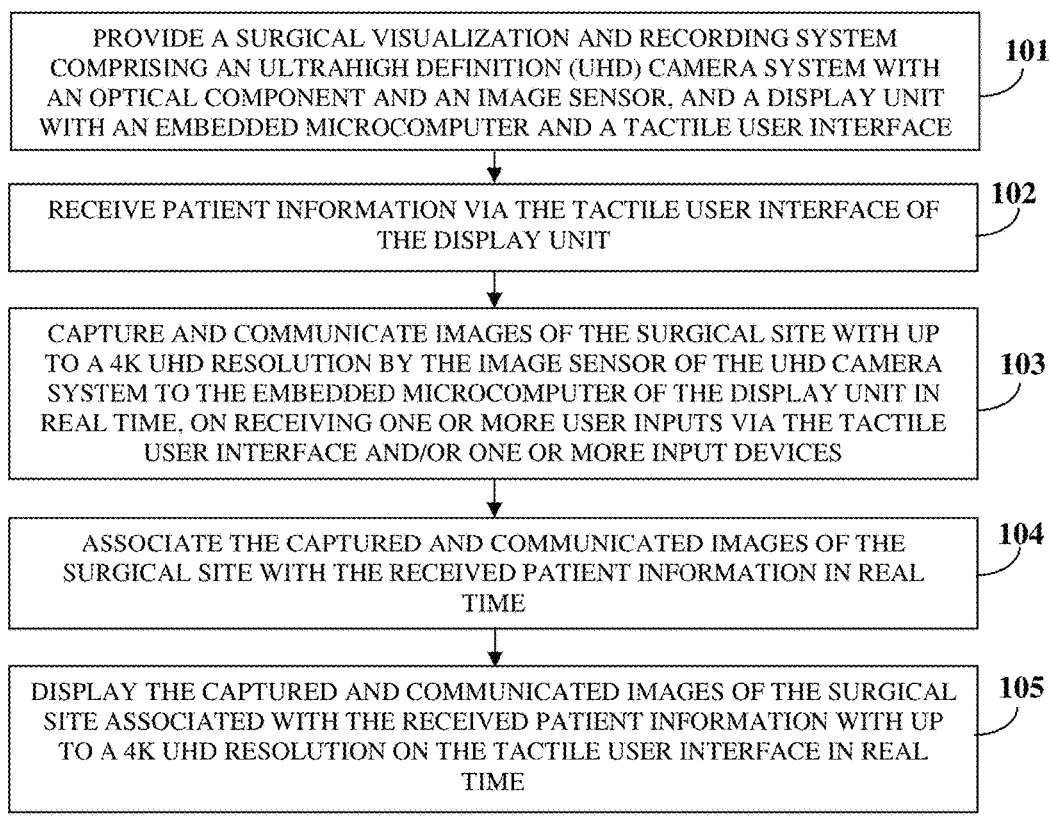
FIG. 1 illustrates a method for capturing, communicating, and displaying images of a surgical site with up to an ultrahigh definition resolution in association with patient information in real time during a surgery.

FIG. 1 illustrates a method for capturing, communicating, and displaying images of a surgical site with up to an ultrahigh definition (UHD) resolution of, for example, 3840 pixels×2160 lines, in association with patient information in real time during a surgery, for example, a minimally invasive surgery such as a laparoscopy. The UHD resolution of 3840 pixels×2160 lines is hereafter referred as "4K UHD resolution". As used herein, the term "images" refers to still images or moving images, for example, videos of the surgical site. Also, as used herein, "surgical site" refers to a location in an organ or a cavity of a patient's body that needs visualization for performing a surgery. In the method disclosed herein, a surgical visualization and recording system (SVRS) comprising a UHD camera system and a display unit is provided 101. The UHD camera system comprises an optical component and an image sensor positioned at a proximal end of a surgical scope device, for example, a laparoscope. As used herein, "optical component" refers to a component that alters a path of light, for example, by focusing or dispersing light by refraction, or by diverging light. The optical component is, for example, an optical lens used for focusing or diverging light. The optical component transmits reflected light from the surgical site to the image sensor. The image sensor is an electronic detector that detects and conveys optical information that constitutes an image. In the method disclosed herein, image parameters are configured on the image sensor for forming the image with up to a 4K UHD resolution. The image sensor receives the reflected light from the surgical site and converts the reflected light into signals, for example, bursts of current that convey the optical information of the surgical site. The image sensor is, for example, a complementary metal-oxide-semiconductor (CMOS) image sensor. The image sensor is in optical communication with the optical component for receiving the reflected light from the surgical site via the optical component and capturing images of the surgical site with up to a 4K UHD resolution. The CMOS image sensor can stream the captured images with up to a 4K UHD resolution, for example, at 30 frames per second (fps) over universal serial bus (USB) interfaces, for example, USB 3.0 interfaces in a compressed motion joint photographic experts group (MJPEG) format to the display unit. The image sensor delivers the captured images in a series of frames to the display unit.

The display unit comprises an embedded microcomputer and a tactile user interface. The embedded microcomputer is in operable communication with the image sensor of the ultrahigh definition (UHD) camera system. The embedded microcomputer comprises at least one processor configured to execute computer program instructions for receiving, transforming, and processing the captured images of the surgical site. In an embodiment, the embedded microcomputer runs, for example, on a Linux® based operating system that hosts a custom software application, hereafter referred as a "surgical visualization and recording application". The surgical visualization and recording application interfaces and communicates with the image sensor of the UHD camera system through an interface, for example, a universal serial bus interface. The embedded microcomputer integrated in the display unit eliminates the need for an external control unit such as an external camera controlled unit and the use of external media in the control unit.

The tactile user interface of the display unit is, for example, a 4K ultrahigh definition (UHD) resolution capacitive touchscreen display interface, in operable communication with the embedded microcomputer for receiving one or more user inputs for controlling operation of the UHD camera system and for displaying the captured images of the surgical site with up to a 4K UHD resolution. The tactile user interface is, for example, an online web interface, a web based downloadable application interface, a mobile based downloadable application interface, etc., that senses and accepts tactile input. In the method disclosed herein, when a user, for example, a surgeon provides patient information to the surgical visualization and recording system (SVRS), for example, by entering the patient information on the tactile user interface of the display unit, the embedded microcomputer receives 102 the patient information via the tactile user interface of the display unit. The patient information comprises, for example, a patient identifier, a patient name, a surgeon name, a type of surgery, a description of the surgery, a date of the surgery, etc. The ability to input patient information in the same integrated custom-built tactile user interface eliminates additional paperwork required to associate the captured images to a patient.

The image sensor of the ultrahigh definition (UHD) camera system captures and communicates 103 images of the surgical site with up to a 4K UHD resolution to the embedded microcomputer of the display unit in real time, on receiving one or more user inputs via the tactile user interface of the display unit and/or one or more input devices operably connected to the display unit through the embedded microcomputer. The input devices are, for example, a keyboard such as an alphanumeric keyboard, a joystick, a pointing device such as a computer mouse, a touch pad, a light pen, a digital pen, a microphone for providing voice input, a digital camera, a physical button, a touch sensitive display device, a track ball, a pointing stick, any device capable of sensing a tactile input, a foot switch, a portable wireless controller, etc. Image parameters are downloaded to the image sensor for capturing and communicating the images of the surgical site with up to a 4K UHD resolution to the embedded microcomputer. The user, for example, the surgeon provides user inputs comprising, for example, an image capture command, an image record command, etc. In an embodiment, the images sensor utilizes a wired mode of communication, for example, a universal serial bus (USB) communication, to communicate the captured images of the surgical site to the embedded microcomputer of the display unit. In another embodiment, the images sensor with built-in custom software utilizes a wireless mode of communication, for example, Bluetooth® of Bluetooth Sig, Inc., Wi-Fi® of Wi-Fi Alliance Corporation, etc., to communicate the captured images of the surgical site to the embedded microcomputer of the display unit. A generic computer using a generic program cannot capture and communicate images of the surgical site with up to a 4K UHD resolution from the image sensor of the UHD camera system to the embedded microcomputer of the display unit in real time, on receiving one or more user inputs via the tactile user interface of the display unit and/or one or more input devices, in accordance with the method steps disclosed above.

The embedded microcomputer receives the captured and communicated images of the surgical site in the ultrahigh definition (UHD) format from the image sensor of the UHD camera system using the surgical visualization and recording application (SVRA). The embedded microcomputer considers the captured and communicated images received from the image sensor of the UHD camera system as final images. The image capture is initiated upon receiving an image capture command from a user through the tactile user interface of the display unit. The embedded microcomputer associates 104 the captured and communicated images of the surgical site with the received patient information in real time. As used herein, associating the captured and communicated images of the surgical site with the received patient information refers to linking or integrating the received patient information to the captured and communicated images of the surgical site. The embedded microcomputer appends the received patient information to the captured and communicated images of the surgical site such that the captured and communicated images can be visualized with up to a 4K UHD resolution along with the received patient information in real time. In an embodiment, the embedded microcomputer overlays the received patient information on the captured and communicated images using image processing techniques. In another embodiment, the image sensor of the UHD camera system delivers data of the images in a series of frames to the embedded microcomputer of the display unit. In case of recording, the embedded microcomputer overlays each frame with the received patient information and stores the frame with the overlaid patient information to a storage location in a file system. A generic computer using a generic program cannot associate the captured and communicated images of the surgical site with the received patient information in real time in accordance with the method steps disclosed above. In an embodiment, the embedded microcomputer, using the SVRA, organizes the captured and communicated images of the surgical site with the received patient information in a file system. For example, the embedded microcomputer stores the captured and communicated images of the surgical site with the received patient information of multiple patients in distinct files within patient folders. The directory structure in the file system for each patient is, for example, Video file name NP_PatientID_MMMDDYYYY_NNN (date format MMMDDYYYY), where NNN is a serial number, for example, 001, 002, 003, . . . , etc.; Image file name NP_PatientID_MMMDDYYYY_NNN, where NNN is a serial number, for example, 001, 002, 003, . . . , etc.; or NP_PatientID_MMMDDYYYY_info.txt for accessing the patient information file. A generic computer using a generic program cannot organize the captured and communicated images of the surgical site with the received patient information in a file system in accordance with the method steps disclosed above.

The display unit of the surgical visualization and recording system (SVRS) displays 105 the captured and communicated images of the surgical site associated with the received patient information with up to a 4K ultrahigh definition (UHD) resolution on the tactile user interface in real time. In an embodiment, the display unit displays the patient information over live images. The display unit, via the tactile user interface, displays information, display interfaces, user interface elements such as swipable arrows, buttons, icons, etc., for example, for receiving user inputs such as an image snap command, a video record command, etc., and for displaying the captured and communicated images of the surgical site associated with the received patient information. In an embodiment, the display unit comprises, for example, a video display, a liquid crystal display, a plasma display, an organic light emitting diode (OLED) based display, etc. Using the surgical visualization and recording application, the embedded microcomputer renders the tactile user interface on the display unit for receiving the user inputs to capture and record the images of the surgical site. The tactile user interface, and in an embodiment, one or more input devices are used for inputting the patient information into the embedded microcomputer and/or for controlling the capture, recording, and the display of the images of the surgical site. In an embodiment, the embedded microcomputer records the captured and communicated images of the surgical site with up to a 4K UHD resolution and with the received patient information in a storage device, for example, a removable drive connected to the display unit, for example, via a universal serial bus interface, in real time.

In an embodiment, a user, for example, a surgeon can trigger the image sensor of the ultrahigh definition (UHD) camera system to capture and communicate the images of the surgical site to the embedded microcomputer and trigger the embedded microcomputer to receive, record, and display the images of the surgical site, by controlling an input device, for example, a foot switch, thereby allowing the surgeon to focus on the surgery instead of triggering the capture, record, and display of the images of the surgical site through an external control unit. In another embodiment, an input device, for example, a handheld or portable wireless controller can be used by the surgeon's technician to trigger the image sensor to capture and communicate the images of the surgical site to the embedded microcomputer and trigger the embedded microcomputer to receive, record, and display the images of the surgical site, thereby allowing the surgeon to focus on the surgery instead of triggering the capture, record, and display of the images of the surgical site through an external control unit. The user inputs entered on the tactile user interface of the display unit are transformed, processed, and executed by an algorithm executed by at least one processor in the embedded microcomputer for controlling the capture, the recording, and the display of the images of the surgical site with up to a 4K UHD resolution and for transmitting the captured and communicated images of the surgical site associated with the received patient information to an external system and/or to a client application on a user device. A generic computer using a generic program cannot display the captured and communicated images of the surgical site associated with the received patient information with up to a 4K UHD resolution on the tactile user interface in real time in accordance with the method steps disclosed above.

In an embodiment, the embedded microcomputer of the display unit securely stores the captured and communicated images of the surgical site with the received patient information on an external system, for example, a hospital system, directly in real time using the built-in surgical visualization and recording application of the embedded microcomputer, without transmission interfaces. A user, for example, a surgeon may connect a storage device, for example, a flash drive, a hard drive, or a network drive on a secure hospital network to the display unit, for example, using universal serial bus (USB) interfaces for recording 4K ultrahigh definition (UHD) images directly to the storage device in real time to preclude unauthorized staff from mishandling and manipulating the patient information associated with the captured and communicated images and to maintain confidentiality of the patient information under the Health Insurance Portability and Accountability Act (HIPAA). The surgical visualization and recording system (SVRS) therefore secures the captured and communicated images of the surgical site with the received patient information in accordance with the HIPAA guidelines. The network drive on the secure hospital network maps to the SVRS for storing the captured and communicated images of the surgical site with the received patient information in the network drive. A generic computer using a generic program cannot securely store the captured and communicated images of the surgical site with the received patient information on an external system directly in real time, without transmission interfaces in accordance with the method steps disclosed above.

In another embodiment, the embedded microcomputer of the display unit stores the captured and communicated images of the surgical site with the received patient information in a cloud computing environment over a network, for example, the internet, in real time. As used herein, "cloud computing environment" refers to a processing environment comprising configurable computing physical and logical resources, for example, networks, servers, storage media, virtual machines, applications, services, etc., and data distributed over a network. The cloud computing environment provides on-demand network access to a shared pool of the configurable computing physical and logical resources. A generic computer using a generic program cannot store the captured and communicated images of the surgical site with the received patient information in a cloud computing environment over a network in real time in accordance with the method steps disclosed above.

The embedded microcomputer controls the capture, the recording, and the display of the images of the surgical site with up to a 4K ultrahigh definition (UHD) resolution, on receiving one or more user inputs via the tactile user interface of the display unit and/or one or more input devices. The user inputs for controlling the display of the images of the surgical site on the tactile user interface of the display unit comprise, for example, a play command, a pause command, and a stop command. In an embodiment, the embedded microcomputer controls one or more of multiple camera parameters of the UHD camera system on receiving one or more user inputs via the tactile user interface of the display unit and/or one or more input devices. The camera parameters comprise, for example, white balance, brightness, sharpness, contrast, gamma, saturation, resolution, gain, exposure, frame rate, etc. In the method disclosed herein, the camera parameters with the patient information is set up using the embedded microcomputer along with the tactile user interface utilizing the surgical visualization and recording application (SVRA), thereby precluding the need for an external control unit for setting up the camera parameters.

In an embodiment, the embedded microcomputer of the display unit transmits the captured and communicated images of the surgical site with up to a 4K ultrahigh definition (UHD) resolution and with the associated patient information in real time to a client application on a user device, for example, a personal computer, a laptop, a tablet computing device, a smartphone, etc., via an internal hospital network for allowing viewing of the captured and communicated images of the surgical site with the received patient information on the user device in real time. The transmission of the captured and communicated images of the surgical site with up to a 4K UHD resolution and with the associated patient information in real time to the client application on the user device facilitates remote accessibility to the captured and communicated images of the surgical site with up to a 4K UHD resolution. The embedded microcomputer transmits the captured and communicated images, for example, a live video associated with the received patient information for viewing over a dedicated wireless channel to a client application, for example, a mobile application, that is loaded on the user device. A generic computer using a generic program cannot transmit the captured and communicated images of the surgical site with up to a 4K UHD resolution and with the received patient information in real time to the client application on the user device via a network for allowing viewing of the captured and communicated images of the surgical site with the received patient information on the user device in real time, in accordance with the method steps disclosed above.

A user, for example, a surgeon can review the captured and communicated images of the surgical site with up to a 4K ultrahigh definition (UHD) resolution on the display unit of the surgical visualization and recording system (SVRS) during the surgery. The embedded microcomputer of the display unit can record the captured and communicated images of the surgical site with the patient information on a storage device, for example, a removable drive, if the storage device is connected to the display unit through the embedded microcomputer. In an embodiment, the embedded microcomputer of the display unit replays the captured and communicated images of the surgical site instantly without additional conversion or re-processing of the captured and communicated images. The resolution of the captured and communicated images of the surgical site is configurable up to a 4K UHD resolution. In an embodiment, the display unit displays the captured and communicated images of the surgical site with up to a 4K UHD resolution on the tactile user interface in real time. In another embodiment, the display unit displays pre-recorded images of the surgical site from a storage device, for example, a removable drive, operably connected to the display unit. The embedded microcomputer receives user inputs, for example, an image capture command, an image record command, a play command, a pause command, a stop command, etc., to control the display of the pre-recorded images of the surgical site. The embedded microcomputer also alters the camera parameters, for example, brightness, contrast, sharpness, gamma, saturation, resolution, gain, exposure, white balance, frame rate, etc., of the pre-recorded images on the display unit based on user inputs.

The surgical visualization and recording system (SVRS) provides the display unit with the tactile user interface for receiving patient information and user inputs. The tactile user interface comprises a defined space for entering the patient information and providing the user inputs, for example, in the form of touch gestures using a stylus or fingers on the tactile user interface. The embedded microcomputer receives these touch gestures as user inputs for receiving images of the surgical site captured and communicated by the image sensor of the ultrahigh definition (UHD) camera system in real time, and in an embodiment, recording the captured and communicated images of the surgical site. In an embodiment, the embedded microcomputer receives the patient information and the user inputs via the client application supported by the SVRS on the user device through the network. The embedded microcomputer distinguishes between an image capture command and an image record command inputted by the user via the tactile user interface. The embedded microcomputer transforms the user inputs on the tactile user interface into an action of triggering the optical component and the image sensor of the UHD camera system to capture and communicate the images of the surgical site to the embedded microcomputer in real time, and in an embodiment, record the captured and communicated images on a storage device. In an embodiment, the embedded microcomputer receives the user inputs via input devices, for example, a portable wireless controller and/or a foot switch operably connected to the display unit. Button presses on the portable wireless controller and/or the foot switch constitute the user inputs provided to the embedded microcomputer. The embedded microcomputer receives these button presses as user inputs and distinguishes between the image capture command and the image record command. The embedded microcomputer transforms the user inputs from the portable wireless controller and/or the foot switch into an action of triggering the optical component and the image sensor of the UHD camera system to capture and communicate the images of the surgical site to the embedded microcomputer in real time, and in an embodiment, record the captured and communicated images on a storage device.

The image sensor of the ultrahigh definition (UHD) camera system transforms the captured images of the surgical site to data that is suitable for communication using a universal serial bus (USB) protocol over a USB cable via a USB interface to the display unit of the surgical visualization and recording system (SVRS). The embedded microcomputer transforms the data into a format that is compatible with the display unit for displaying the captured and communicated images of the surgical site on the tactile user interface, without affecting the resolution. The embedded microcomputer associates the captured and communicated images of the surgical site with the patient information, and therefore, in an embodiment, transforms the captured and communicated images into resultant images integrated with the patient information to allow the captured and communicated images of the surgical site and the patient information to be visualized together without affecting the visibility and the quality of the captured and communicated images of the surgical site. The method steps 101, 102, 103, 104, and 105 disclosed above performed by the SVRS are tangible, provide useful results, and are not abstract. The operable coupling of the UHD camera system to the surgical scope device and the display unit with the embedded microcomputer and the tactile user interface and communication between the UHD camera system and the display unit with the external system and the client application on the user device for displaying the captured and communicated images of the surgical site associated with the received patient information with up to a 4K UHD resolution are improvements in surgical visualization technology.

Moreover, the embedded microcomputer receives user inputs in the form of touch gestures via the tactile user interface, and/or in the form of button presses on input device, for example, the portable wireless controller and/or the foot switch for controlling the camera parameters comprising, for example, brightness, contrast, sharpness, gain, exposure, frame rate, etc. The embedded microcomputer receives these user inputs and distinguishes the user inputs inputted for the different camera parameters. The embedded microcomputer transforms these user inputs into an action of controlling or modifying the camera parameters for triggering the capture of the images of the surgical site by the image sensor of the ultrahigh definition (UHD) camera system in real time, and in an embodiment, recording the captured images. Furthermore, the embedded microcomputer receives user inputs, for example, an image capture command, an image record command, a play command, a pause command, and a stop command in the form of touch gestures via the tactile user interface, and/or in the form of button presses on the input devices, for example, the portable wireless controller and/or the foot switch for controlling the capture, the recording, and the display of the images of the surgical site. The embedded microcomputer receives these user inputs and distinguishes the user inputs for controlling the capture, the recording, and the display of the images. The embedded microcomputer transforms these user inputs into an action of controlling the capture, the recording, and the display of the images of the surgical site.

Consider an example where a surgeon performs a laparoscopy using the surgical visualization and recording system (SVRS) disclosed herein. The surgeon connects the ultrahigh definition (UHD) camera system to the display unit with the built-in embedded microcomputer via communication interfaces, for example, universal serial bus (USB) interfaces. The surgeon activates the SVRS to access the tactile user interface of the display unit. The surgeon enters the patient information comprising, for example, a patient identifier, the patient's name, the surgeon's name, type of the surgery, and a brief description of the surgical problem on the tactile user interface. The surgeon or a technician then sets up and verifies the camera parameters, for example, brightness, contrast, sharpness, gamma, saturation, gain, exposure, white balance, etc., of the UHD camera system via the tactile user interface. After inputting the camera parameters and the patient information, during the surgery, the surgeon or the technician triggers capture of images, for example, still images or videos of the surgical site via the tactile user interface. The surgeon or the technician may also trigger the capture of the images using an input device, for example, a foot switch operably connected to the display unit. The SVRS allows the surgeon to capture, record, and pause the images with up to a 4K UHD resolution set up by the surgeon. The SVRS allows these captured images to be stored on a predefined network drive on a hospital network along with a patient information file related to the surgery, thereby eliminating the mishandling and manipulation of surgical data, and allowing this surgical data to be secured in accordance with Health Insurance Portability and Accountability (HIPAA) guidelines.

In an embodiment, the surgical visualization and recording system (SVRS) receives instructions from a user to capture multiple images. The image sensor of the ultrahigh definition (UHD) camera system captures and communicates multiple images to the embedded microcomputer of the display unit, which stores the captured and communicated images to a storage location in a file system with a date and a time stamp. In another embodiment, the SVRS receives instructions from a user to capture a single image of the surgical site. The image sensor captures and communicates the single image to the embedded microcomputer of the display unit, which stores the captured and communicated single image to a storage location in a file system with a date and a time stamp. In an embodiment, this storage path can also be set on an external universal serial bus (USB) drive if required by the surgeon. The SVRS allows the surgeon to view the captured and communicated images in the same integrated tactile user interface. In an embodiment, the SVRS transmits a live video of the surgical site over a dedicated wireless channel from the embedded microcomputer of the display unit to a mobile application that can be loaded on a hospital tablet for viewing. The SVRS thus eliminates the need for multiple accessories and provides an integrated end to end technology solution for process issues faced in an endoscopic surgery.

In the method disclosed herein, the design and the flow of information between the optical component and the image sensor of the ultrahigh definition (UHD) camera system of the surgical visualization and recording system (SVRS), between the tactile user interface and the embedded microcomputer of the display unit of the SVRS, and between the embedded microcomputer, the input devices, the external system, and the client application on the user device are deliberate, designed, and directed. Every user input provided to the embedded microcomputer through the tactile user interface of the display unit and/or through one or more input devices, is configured by the embedded microcomputer to steer the user towards a finite set of predictable outcomes. The embedded microcomputer implements one or more specific computer programs to direct the user towards a set of end results. The interactions designed by the SVRS allow the SVRS to receive the patient information and the user inputs from the user, and from this information, using other, separate and autonomous computer programs, capture, communicate, record, and display images of the surgical site with up to a 4K ultrahigh definition (UHD) resolution in association with the patient information in real time during the surgery. To receive the patient information via the tactile user interface of the display unit, capture and communicate the images of the surgical site with up to a 4K UHD resolution to the embedded microcomputer in the display unit in real time on receiving user inputs via the tactile user interface of the display unit and/or via one or more input devices, associate the captured and communicated images of the surgical site with the received patient information in real time, and display the captured and communicated images of the surgical site associated with the received patient information with up to a 4K UHD resolution on the tactile user interface in real time requires four or more separate computer programs and subprograms, the execution of which cannot be performed using a generic computer with a generic program.

The method disclosed herein provides an improvement in surgical visualization technology as follows. On implementing the method disclosed herein, the image sensor of the ultrahigh definition (UHD) camera system of the surgical visualization and recording system (SVRS) captures and communicates images of the surgical site with up to a 4K UHD resolution to the embedded microcomputer of the display unit of the SVRS in real time, on receiving one or more user inputs via the tactile user interface of the display unit and/or one or more input devices. The embedded microcomputer receives the patient information via the tactile user interface of the display unit. The embedded microcomputer associates the captured and communicated images of the surgical site with the received patient information in real time. The display unit of the SVRS displays the captured and communicated images of the surgical site associated with the received patient information with up to a 4K UHD resolution on the tactile user interface in real time. The SVRS allows a user, for example, a surgeon who performs the minimally invasive surgery to access to the patient information, for example, name, age, gender, patient identifier, medical history, details about the minimally invasive surgery to be performed, etc., prior to, during, at any instance, and after the minimally invasive surgery. The access to the patient information along with visualization of the captured and communicated images of the surgical site in real time allows the surgeon to plan and conduct the surgery with enhanced visualization and information in real time.

Moreover, the surgical visualization and recording system (SVRS) provides a single display unit for displaying the captured and communicated images of the surgical site with up to a 4K ultrahigh definition (UHD) resolution in real time without a need for an external media viewer. The SVRS comprises the embedded microcomputer within the display unit unlike a conventional surgical visualization system that comprise separate, spaced apart components, for example, a camera assembly, an external control unit, and an external monitor. The absence of an external control unit in the SVRS reduces power consumption of the SVRS and reduces transmission losses of the communicated images of the surgical site. The camera parameters of the captured and communicated images of the surgical site can be controlled by the user inputs that are received via the tactile user interface, thereby eliminating the risk of division of concentration of the surgeon to control the camera parameters using an external control unit and to visualize the surgical site on the display unit. The SVRS securely stores the captured and communicated images of the surgical site directly on the external system to meet the Health Insurance Portability and Accountability (HIPAA) guidelines. The direct storage of the captured and communicated images of the surgical site eliminates the risk of mishandling and manipulation of the captured and communicated images of the surgical site and the associated patient information by unauthorized individuals. Furthermore, the SVRS stores the captured and communicated images of the surgical site in a cloud computing environment. Furthermore, the SVRS provides remote accessibility of the captured and communicated images of the surgical site with the patient information by transmitting the captured and communicated images of the surgical site with the patient information to the client application on the user device, thereby allowing another user to view the captured and communicated images of the surgical site in real time and review the recorded images of the surgical site.

The focus of the method and the surgical visualization and recording system (SVRS) disclosed herein is an improvement to surgical visualization technology itself, and not on economic or other tasks for which a generic computer is used in its ordinary capacity. Accordingly, the method and the SVRS disclosed herein are not directed to an abstract idea. Rather, the method and the SVRS disclosed herein are directed to a specific improvement to the way the components of the SVRS operate, embodied in, for example, receiving the patient information via the tactile user interface, capturing and communicating the images of the surgical site with up to a 4K ultrahigh definition (UHD) resolution to the embedded microcomputer of the display unit in real time on receiving user inputs, associating the captured and communicated images of the surgical site with the received patient information in real time, and displaying the captured and communicated images of the surgical site associated with the received patient information with up to a 4K UHD resolution on the tactile user interface in real time.

Figure 2:
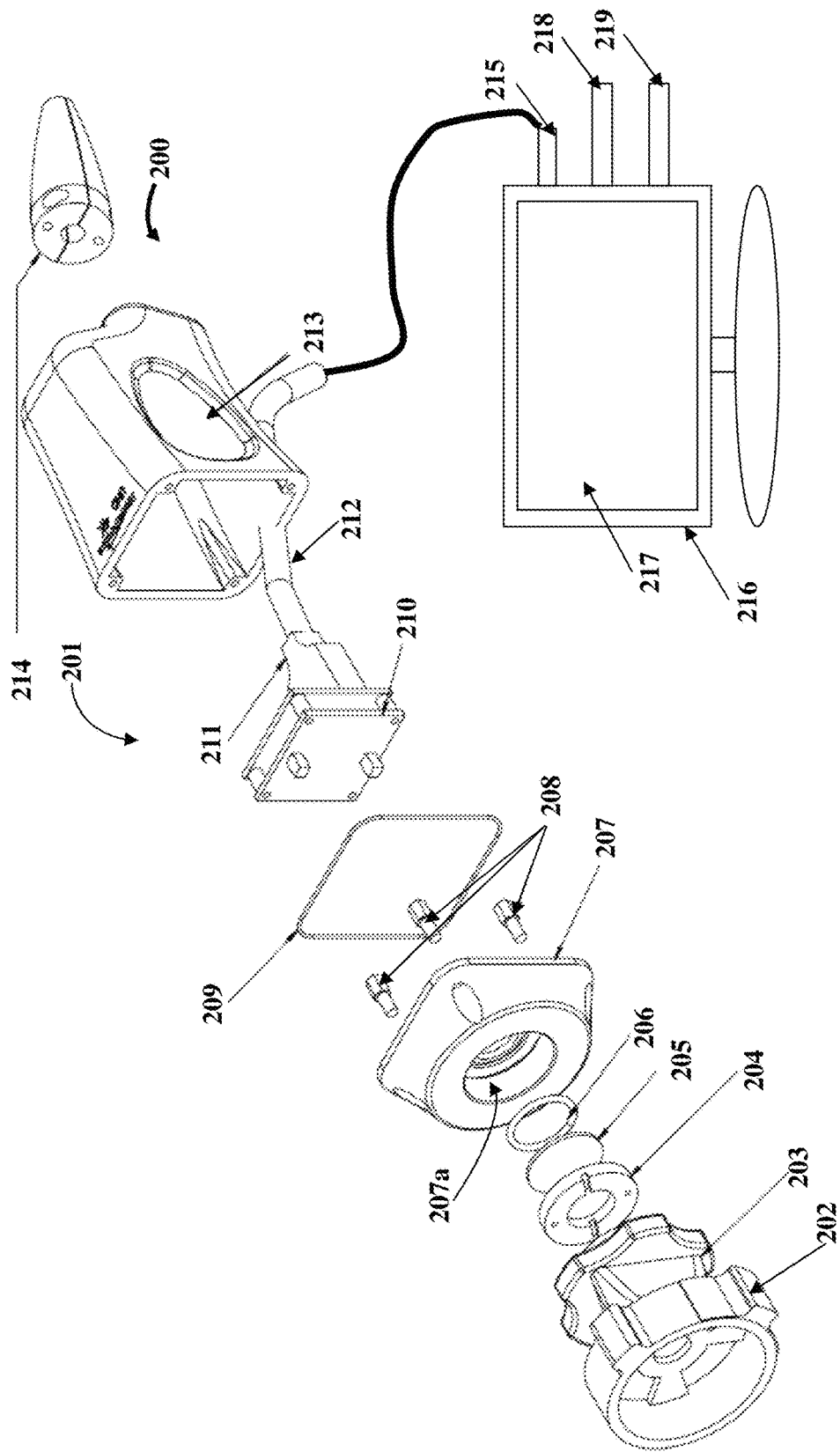
FIG. 2 exemplarily illustrates a perspective exploded view of a surgical visualization and recording system for capturing, communicating, and displaying images of a surgical site with up to an ultrahigh definition resolution in association with patient information in real time during a surgery.

FIG. 2 exemplarily illustrates a perspective exploded view of a surgical visualization and recording system (SVRS) 200 for capturing, communicating, and displaying images of a surgical site with up to a 4K ultrahigh definition (UHD) resolution in association with patient information in real time during a surgery. The SVRS 200 comprises the ultrahigh definition (UHD) camera system 201 with the optical component 203 and a camera interface board 210 accommodating the image sensor 220 exemplarily illustrated in FIG. 3, and the display unit 216 comprising the tactile user interface 217 and the embedded microcomputer 222 exemplarily illustrated in FIG. 3, as disclosed in the detailed description of FIG. 1. The UHD camera system 201 further comprises a C-mount interface 202, a lock ring 204, a glass 205, an O-ring 206, a camera head 207, one or more studs 208, a gasket 209, a universal serial bus (USB) cable 212, a USB interface connector 211, and a cable gland 214. The UHD camera system 201 is enclosed in a housing 213. The C-mount interface 202 is a lens mount assembly that connects to the optical component 203 and allows adjustment of the focal length of the optical component 203. The C-mount interface 202 is operably coupled to the optical component 203 for adjusting the focal length of the optical component 203, for example, from about 18 millimeters (mm) to about 35 mm. The lock ring 204 is a threaded washer used for securing the position of the optical component 203 onto the camera head 207. The lock ring 204 prevents inadvertent movement and loosening of the optical component 203 from the camera head 207 and seals the gaps between the optical component 203 and the camera head 207 to provide a watertight sealing.

The glass 205 of the ultrahigh definition (UHD) camera system 201 is refractive and is designed to provide focus and/or zoom. The glass 205 is operably coupled to the C-mount interface 202 to adjust the optical component 203 to focal lengths ranging, for example, from about 18 mm to about 35 mm. The optical component 203 is sealed with the O-ring 206 and the gasket 209. The O-ring 206 is positioned between the glass 205 and the camera head 207 and compressed in a groove 207a of the camera head 207 to absorb shock and vibration. The camera head 207 houses the C-mount interface 202, the optical component 203, the lock ring 204, the glass 205, and the O-ring 206. The studs 208 securely attach the camera head 207 to the camera interface board 210. The gasket 209 provides a seal between the camera head 207 and the housing 213 and absorbs shock and vibration. The camera interface board 210 is securely housed in the housing 213 and the camera head 207 is attached to the housing 213 using the studs 208. The image sensor 220 accommodated in the camera interface board 210 of the UHD camera system 201 captures and communicates images of the surgical site with up to a 4K UHD resolution to the embedded microcomputer 222 of the display unit 216 in real time as disclosed in the detailed description of FIG. 1.

The universal serial bus (USB) cable 212 is connected to the camera interface board 210 by the USB interface connector 211. The USB cable 212 is used to communicate the captured images of the surgical site to the embedded microcomputer 222 of the display unit 216, where the captured and communicated images of the surgical site are associated with the patient information received via the tactile user interface 217, and displayed with up to a 4K UHD resolution on the tactile user interface 217. The cable gland 214 attaches and secures an end of a cable to the UHD camera system 201. The USB cable 212 is connected to the display unit 216 by a USB interface connector 215. The display unit 216 receives the captured and communicated images of the surgical site via the USB cable 212 and processes the captured and communicated images using the embedded microcomputer 222 to display the captured and communicated images of the surgical site with up to a 4K UHD resolution and with the associated patient information in real time. The USB interface connector 219 is used for connecting the display unit 216 to input devices, for example, a foot switch, for controlling the capture, recording, and display of the captured and communicated images of the surgical site with the associated patient information. The input devices can also control the display of the pre-recorded images of the surgical site from a storage device, for example, a removable drive 218 operably connected to the display unit 216.

Figure 3:
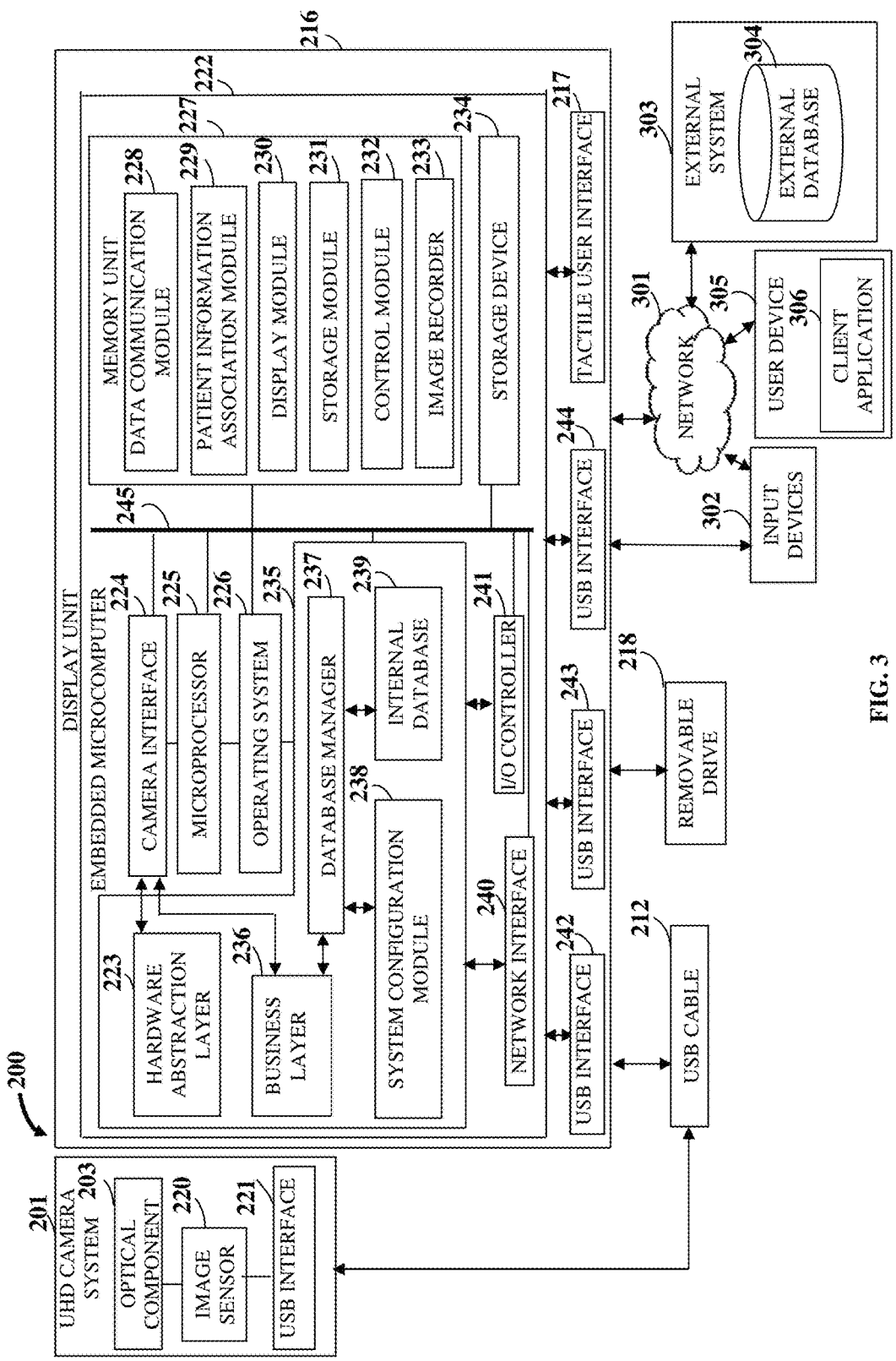
FIG. 3 exemplarily illustrates a block diagram of the surgical visualization and recording system for capturing, communicating, and displaying images of a surgical site with up to an ultrahigh definition resolution in association with patient information in real time during a surgery.

FIG. 3 exemplarily illustrates a block diagram of the surgical visualization and recording system (SVRS) 200 for capturing, communicating, and displaying images of a surgical site with up to a 4K ultrahigh definition (UHD) resolution in association with patient information in real time during a surgery. The SVRS 200 comprises the UHD camera system 201 with the optical component 203 and the image sensor 220, and the display unit 216 with the tactile user interface 217 and the embedded microcomputer 222 as disclosed in the detailed description of FIGS. 1-2. The UHD camera system 201 is waterproof. The UHD camera system 201 is made of waterproof materials comprising, for example, polypropylene, polyetherimide, polychlorotrifluoroethylene, etc. The optical component 203 is positioned at a proximal end of a surgical scope device. The optical component 203 optically communicates with the image sensor 220. The camera interface board 210 exemplarily illustrated in FIG. 2, accommodates the image sensor 220. The image sensor 220 captures the images of the surgical site. The camera interface board 210 comprises a communication interface, for example, a universal serial bus (USB) interface 221 for allowing communication with the display unit 216, for example, using the USB cable 212. In an embodiment, the camera interface board 210 is configured as a 4K complementary metal-oxide-semiconductor (CMOS) camera board with the USB interface 221. The USB interface 221 allows streaming of the captured images with up to a 4K UHD resolution in a 4K UHD digital display format from the image sensor 220 of the UHD camera system 201 to the display unit 216, and/or an external system 303, and/or a cloud computing environment in real time. The image sensor 220 captures and communicates the images of the surgical site with up to a 4K UHD resolution in a compressed motion joint photographic experts group (MJPEG) format to the embedded microcomputer 222 of the display unit 216 via the USB interface 221, for example, a USB 3.0 interface and the USB cable 212, for example, a USB 3.0 cable, in real time.

The display unit 216 is in operable communication with the ultrahigh definition (UHD) camera system 201. The tactile user interface 217 of the display unit 216 receives one or more user inputs for controlling the operation of the UHD camera system 201, for receiving patient information from a user, for example, a surgeon performing a minimally invasive surgery at a surgical site, and for displaying the captured and communicated images of the surgical site with up to a 4K UHD resolution. In an embodiment, the embedded microcomputer 222 of the display unit 216 activates the UHD camera system 201 upon receiving user inputs via the tactile user interface 217 of the display unit 216. The embedded microcomputer 222 invokes the surgical visualization and recording application on the tactile user interface 217 of the display unit 216 for receiving patient information and/or one or more user inputs to control the UHD camera system 201. The embedded microcomputer 222 operably communicates with the image sensor 220 of the UHD camera system 201 and the tactile user interface 217 of the display unit 216. The embedded microcomputer 222 activates the image sensor 220 of the UHD camera system 201 for receiving reflected light from the surgical site via the optical component 203 and capturing and communicating images of the surgical site with up to a 4K UHD resolution to the embedded microcomputer 222 in real time on receiving one or more inputs from the tactile user interface 217 and/or from other input devices 302. The embedded microcomputer 222 activates the tactile user interface 217 for displaying the captured and communicated images of the surgical site with up to a 4K UHD resolution along with the patient information in real time. The embedded microcomputer 222 is a computer system that is programmable using a high level computer programming language. The embedded microcomputer 222 comprises programmed and purposeful hardware. The embedded microcomputer 222 comprises a camera interface 224 that connects with the image sensor 220 of the UHD camera system 201 via a hardware abstraction layer 223. The hardware abstraction layer 223 is a programming layer that allows an operating system 226 of the embedded microcomputer 222 to interact with the optical component 203 and the image sensor 220 of the UHD camera system 201. The camera interface 224 implements the communication between the image sensor 220 and the embedded microcomputer 222. The camera interface 224 connects to the image sensor 220 via the hardware abstraction layer 223 and provides an output, for example, the images captured by the image sensor 220 to a microprocessor 225 of the embedded microcomputer 222 for further processing.

The embedded microcomputer 222 comprises a non-transitory computer readable storage medium, for example, the memory unit 227 for storing program instructions, applications, and data, and at least one processor, for example, the microprocessor 225 communicatively coupled to the non-transitory computer readable storage medium. As used herein, "non-transitory computer readable storage medium" refers to all computer readable media, for example, non-volatile media, volatile media, and transmission media, except for a transitory, propagating signal. Non-volatile media comprise, for example, solid state drives, optical discs or magnetic disks, and other persistent memory volatile media including a dynamic random access memory (DRAM), which typically constitute a main memory. Volatile media comprise, for example, a register memory, a processor cache, a random access memory (RAM), etc. Transmission media comprise, for example, coaxial cables, copper wire, fiber optic cables, modems, etc., including wires that constitute a system bus coupled to the microprocessor 225. The memory unit 227 is configured to store computer program instructions defined by modules, for example, 228, 229, 230, 231, 232, 233, etc., of the embedded microcomputer 222. The modules of the embedded microcomputer 222 are installed and stored in the memory unit 227 of the embedded microcomputer 222. The memory unit 227 is, for example, a random access memory (RAM) or another type of dynamic storage device that stores information and instructions for execution by the microprocessor 225. The memory unit 227 also stores temporary variables and other intermediate information used during execution of the computer program instructions by the microprocessor 225. The embedded microcomputer 222 further comprises a read only memory (ROM) or another type of static storage device that stores static information and instructions for the microprocessor 225.

The microprocessor 225 is configured to execute computer program instructions defined by the modules, for example, 228, 229, 230, 231, 232, 233, etc., of the embedded microcomputer 222 for receiving, transforming, and processing images of a surgical site captured by the image sensor 220. The microprocessor 225 refers to any one or more processors, central processing unit (CPU) devices, finite state machines, computers, microcontrollers, digital signal processors, logic, a logic device, a user circuit, an application specific integrated circuit (ASIC), a field-programmable gate array (FPGA), a chip, etc., or any combination thereof, capable of executing computer programs or a series of commands, instructions, or state transitions. In an embodiment, the microprocessor 225 is implemented as a processor set comprising, for example, a programmed microprocessor and a math or graphics co-processor. The microprocessor 225 is selected, for example, from the Intel® processors such as the Intel® Core i5 processor, the Intel® Core i7 processor, the Itanium® microprocessor, the Pentium® processors, etc., Advanced Micro Devices (AMD®) processors such as the Athlon® processor, UltraSPARC® processors, microSPARC® processors, Hp® processors, International Business Machines (IBM®) processors such as the PowerPC® microprocessor, the MIPS® reduced instruction set computer (RISC) processor of MIPS Technologies, Inc., RISC based computer processors of ARM Holdings, Motorola® processors, Qualcomm® processors, etc. The embedded microcomputer 222 is not limited to employing the microprocessor 225. In an embodiment, the embedded microcomputer 222 employs a controller or a microcontroller. The microprocessor 225 executes the modules, for example, 228, 229, 230, 231, 232, 233, etc., of the embedded microcomputer 222.

As exemplarily illustrated in FIG. 3, the embedded microcomputer 222 further comprises a data bus 245, an input/output (I/O) controller 241, and a network interface 240. The data bus 245 permits communications between the modules, for example 224, 225, 226, 227, 234, 235, 240, 241, etc., of the embedded microcomputer 222. The I/O controller 241 controls input actions and output actions performed by the embedded microcomputer 222. The network interface 240 enables connection of the display unit 216 to a network 301, for example, a short range network or a long range network. In an embodiment, the network interface 240 is provided as an interface card also referred to as a line card on the embedded microcomputer 222. The network interface 240 is, for example, an interface implementing Wi-Fi® of Wi-Fi Alliance Corporation and/or a local area network interface. In an embodiment, the network interface 240 is, for example, one or more of an infrared interface, a FireWire® interface of Apple Inc., an Ethernet interface, a frame relay interface, a cable interface, a digital subscriber line interface, a token ring interface, a peripheral controller interconnect interface, a wide area network interface, interfaces using serial protocols, interfaces using parallel protocols, Ethernet communication interfaces, asynchronous transfer mode interfaces, a high speed serial interface, a fiber distributed data interface, interfaces based on transmission control protocol/internet protocol, interfaces based on wireless communications technology such as satellite technology, radio frequency technology, near field communication, etc.

The network 301 is, for example, one of the internet, an intranet, a wired network, a wireless network, a communication network that implements Bluetooth® of Bluetooth Sig, Inc., a network that implements Wi-Fi® of Wi-Fi Alliance Corporation, an ultra-wideband communication network (UWB), a wireless universal serial bus (USB) communication network, a communication network that implements ZigBee® of ZigBee Alliance Corporation, a general packet radio service (GPRS) network, a mobile telecommunication network such as a global system for mobile (GSM) communications network, a code division multiple access (CDMA) network, a third generation (3G) mobile communication network, a fourth generation (4G) mobile communication network, a fifth generation (5G) mobile communication network, a long-term evolution (LTE) mobile communication network, a public telephone network, etc., a local area network, a wide area network, an internet connection network, an infrared communication network, etc., or a network formed from any combination of these networks. In an embodiment, the captured and communicated images of the surgical site are accessible to users, for example, through a broad spectrum of technologies and devices such as cellular phones, tablet computing devices, etc., with access to the internet.

The embedded microcomputer 222 further comprises modules, for example, a data communication module 228, a patient information association module 229, and a display module 230 stored in the memory unit 227. The data communication module 228 receives patient information via the tactile user interface 217 of the display unit 216 and one or more user inputs for controlling the operation of the ultrahigh definition (UHD) camera system 201 via the tactile user interface 217 and/or one or more input devices 302, for example, a foot switch, a portable wireless controller, etc. The data communication module 228 receives the captured and communicated images of the surgical site with up to a 4K UHD resolution from the image sensor 220 of the UHD camera system 201 in real time. In an embodiment, the embedded microcomputer 222 further comprises storage module 231 for storing the received patient information in an internal database 239, and in an embodiment, in a storage device 234, for example, a hard disk drive, a solid state drive, a solid state hybrid drive, etc., of the embedded microcomputer 222. In another embodiment, the storage module 231 stores the captured and communicated images of the surgical site in the storage device 234.

The patient information association module 229 associates the captured and communicated images of the surgical site with the received patient information, for example, by linking, integrating, or overlaying the received patient information with the captured and communicated images of the surgical site in real time. In an embodiment, the patient information association module 229 organizes the captured and communicated images of the surgical site with the received patient information in a file system. The display module 230 displays the captured and communicated images of the surgical site associated with the received patient information with up to a 4K ultrahigh definition (UHD) resolution on the tactile user interface 217 of the display unit 216 in real time.

In an embodiment, the storage module 231 of the embedded microcomputer 222 securely stores the captured and communicated images of the surgical site with the received patient information in an external database 304, for example, a hospital database, on an external system 303 directly in real time. The internal database 239 and the external database 304 refer to any storage area or medium that can be used for storing data and files. The internal database 239 and the external database 304 can be, for example, any of a structured query language (SQL) data store or a not only SQL (NoSQL) data store such as the Microsoft® SQL Server®, the Oracle® servers, the MySQL® database of MySQL AB Limited Company, the mongoDB® of MongoDB, Inc., the Neo4j graph database of Neo Technology Corporation, the Cassandra database of the Apache Software Foundation, the HBase® database of the Apache Software Foundation, etc. In an embodiment, the internal database 239 and the external database 304 can also be a location on a file system. In another embodiment, the internal database 239 can be remotely accessed by the embedded microcomputer 222 via the network 301. In another embodiment, the internal database 239 and/or the external database 304 are configured as cloud based databases implemented in a cloud computing environment, where computing resources are delivered as a service over the network 301.

The captured and communicated images of the surgical site with the received patient information of multiple patients are stored in the external database 304 in distinct files within each patient's folder. The captured and communicated images of the surgical site with the associated patient information are stored in the external database 304 of the external system 303 directly to avoid mishandling and manipulation of the captured and communicated images of the surgical site with the associated patient information, thereby securing the captured and communicated images of the surgical site with the associated patient information in accordance with the Health Insurance Portability and Accountability (HIPAA) guidelines. In an embodiment, the captured and communicated images of the surgical site with the received patient information are stored in a removable drive 218, for example, a universal serial bus (USB) flash drive. The storage module 231 of the embedded microcomputer 222 therefore stores the captured and communicated images in the internal database 239, and/or in the storage device 234 of the embedded microcomputer 222, and/or in the removable drive 218, and/or in the external database 304. In an embodiment, the embedded microcomputer 222 further comprises an image recorder 233 stored in the memory unit 227 for recording the captured and communicated images of the surgical site with up to a 4K ultrahigh definition (UHD) resolution and with the received patient information in the storage device 234 and/or the removable drive 218 in real time. In an embodiment, the data communication module 228 of the embedded microcomputer 222 receives one or more user inputs for controlling the recording of the captured and communicated images of the surgical site with the associated patient information in the storage device 234 and/or the removable drive 218 in real time, via the tactile user interface 217 and/or one or more input devices 302. In another embodiment, the storage module 231 of the embedded microcomputer 222 stores the captured and communicated images of the surgical site with the received patient information in a cloud computing environment over the network 301 in real time.

In an embodiment, the data communication module 228 of the embedded microcomputer 222 transmits the captured and communicated images of the surgical site with up to a 4K ultrahigh definition (UHD) resolution and with the received patient information in real time to a client application 306, for example, a mobile application, deployed on a user device 305 via the network 301 for allowing viewing of the captured and communicated images of the surgical site with the received patient information on the user device 305 in real time. The user device 305 communicates with the surgical visualization and recording system 200 via the network 301. The user device 305 is an electronic device, for example, one or more of a personal computer, a tablet computing device, a mobile computer, a mobile phone, a smartphone, a portable computing device, a personal digital assistant, a laptop, a wearable computing device such as the Google Glass® of Google Inc., the Apple Watch® of Apple Inc., the Android Smartwatch® of Google Inc., etc., a touch centric device, a workstation, a server, a client device, a portable electronic device, a network enabled computing device, an interactive network enabled communication device, a television, an image capture device, a web browser, any other suitable computing equipment, combinations of multiple pieces of computing equipment, etc. In an embodiment, the embedded microcomputer 222 further comprises a control module 232 stored in the memory unit 227. The control module 232 controls the capture, the recording, and the display of the images of the surgical site with up to an 4K ultrahigh definition (UHD) resolution, on receiving one or more user inputs via the tactile user interface 217 of the display unit 216 and/or one or more of the input devices 302. In an embodiment, the control module 232 controls one or more of multiple camera parameters comprising, for example, white balance, brightness, sharpness, contrast, gamma, saturation, resolution, gain, exposure, frame rate, etc., of the UHD camera system 201, on receiving one or more user inputs via the tactile user interface 217 of the display unit 216 and/or one or more of the input devices 302. In an embodiment, the data communication module 228, the patient information association module 229, the display module 230, the storage module 231, the control module 232, and the image recorder 233 constitute the surgical visualization and recording application of the embedded microcomputer 222.

Computer applications and programs are used for operating the embedded microcomputer 222. The programs are loaded onto the storage device 234 and into the memory unit 227. In an embodiment, the computer applications and programs are loaded into the memory unit 227 directly via the network 301. Computer applications and programs are executed by double clicking a related icon displayed on the tactile user interface 217 of the display unit 216 using one of the input devices 302 or a touch gesture on the tactile user interface 217.

The microprocessor 225 of the embedded microcomputer 222 executes the operating system 226 selected, for example, from the Linux® operating system, the Ubuntu® operating system of Canonical Limited, a simplified Linux® setup, the Unix® operating system, any version of the Microsoft® Windows® operating system, the Mac OS of Apple Inc., the IBM® OS/2, VxWorks® of Wind River Systems, Inc., QNX Neutrino® developed by QNX Software Systems Ltd., the Palm OS®, the Solaris operating system developed by Sun Microsystems, Inc., the Android® operating system of Google Inc., the Windows Phone® operating system of Microsoft Corporation, the BlackBerry® operating system of BlackBerry Limited, the iOS operating system of Apple Inc., the Symbian™ operating system of Symbian Foundation Limited, etc. The embedded microcomputer 222 employs the operating system 226 for performing multiple tasks. The operating system 226 manages and coordinates activities and sharing of resources of the embedded microcomputer 222. The operating system 226 further manages security of the ultrahigh definition (UHD) camera system 201 and the display unit 216, peripheral devices connected to the UHD camera system 201 and the display unit 216, and network connections. The operating system 226 on the embedded microcomputer 222 executes different programs using the microprocessor 225. The microprocessor 225 and the operating system 226 together define a computer platform for which application programs in high level programming languages are written.

Additional software components 235 of the embedded microcomputer 222 comprise the hardware abstraction layer 223 as disclosed above, a system configuration module 238, the internal database 239, a database manager 237, and a business layer 236. The system configuration module 238 associates setup parameters for the patient. The internal database 239 stores the captured and communicated images of the surgical site with the received patient information in real time. The storage of the captured and communicated images of the surgical site with the associated patient information in the internal database 239 provides an instant review of the captured and communicated images of the surgical site with the associated patient information on the display unit 216 to the user during the surgery. In an embodiment, the captured and communicated images of the surgical site with the received patient information of multiple patients are stored in the internal database 239 in distinct files within respective patient folders. The database manager 237 manages patient information that is stored in the internal database 239. The database manager 237 manages functionalities of the internal database 239 comprising, for example, creation and maintenance of the internal database 239. The database manager 237 creates the internal database 239, backs up the internal database 239, restores the internal database 239, clones the internal database 239, renames the internal database 239, etc. In an embodiment, the database manager 237 discovers and manages the external database 304 in the external system 303 remotely via the network 301. The database manager 237 connects to the external database 304 and displays information from catalogs that are a part of the external database 304. The database manager 237 initiates features and functions that are external to a user interface provided for managing a remote database. The business layer 236 implements business logic that determines how data is created, stored, and changed in the surgical visualization and recording system 200. The business layer 236 comprises business rules and workflows. The business rules describe a specific procedure and the workflow comprises procedural steps, required input and output information, and tools required for each step of the specific procedure. The business layer 236 determines the sequence of operations associated with data in the internal database 239 for executing the business rules.

The microprocessor 225 retrieves instructions defined by the data communication module 228, the patient information association module 229, the display module 230, the storage module 231, the control module 232, the image recorder 233, and the additional software components 235 for performing respective functions disclosed above. The microprocessor 225 retrieves instructions for executing the modules, for example, 228, 229, 230, 231, 232, 233, etc., of the embedded microcomputer 222 from the memory unit 227. A program counter determines the location of the instructions in the memory unit 227. The program counter stores a number that identifies the current position in the program of each of the modules, for example, 228, 229, 230, 231, 232, 233, etc., of the embedded microcomputer 222. The instructions fetched by the microprocessor 225 from the memory unit 227 after being processed are decoded. The instructions are stored in an instruction register in the microprocessor 225. After processing and decoding, the microprocessor 225 executes the instructions, thereby performing one or more processes defined by those instructions.

At the time of execution, the instructions stored in the instruction register are examined to determine the operations to be performed. The microprocessor 225 then performs the specified operations. The operations comprise arithmetic operations and logic operations. The operating system 226 performs multiple routines for performing several tasks required for executing the modules, for example, 228, 229, 230, 231, 232, 233, etc., of the embedded microcomputer 222. The tasks performed by the operating system 226 comprise, for example, assigning memory to the modules, for example, 228, 229, 230, 231, 232, 233, etc., of the embedded microcomputer 222 and to data used by the embedded microcomputer 222, moving data between the memory unit 227 and disk units, and handling input/output operations. The operating system 226 performs the tasks on request by the operations and after performing the tasks, the operating system 226 transfers the execution control back to the microprocessor 225. The microprocessor 225 continues the execution to obtain one or more outputs. The outputs of the execution of the modules, for example, 228, 229, 230, 231, 232, 233, etc., of the embedded microcomputer 222 are displayed to the user on the display unit 216, and in an embodiment, on the user device 305.

In the surgical visualization and recording system (SVRS) 200 disclosed herein, the ultrahigh definition (UHD) camera system 201 interfaces with a surgical scope device (not shown in FIG. 3), the display unit 216, the user device 305, and the external system 303 to implement the capture, record, display, and communication of the images of a surgical site with up to a 4K UHD resolution in association with patient information in real time during a surgery. The display unit 216 comprising the tactile user interface 217 and the embedded microcomputer 222 operably communicates with the UHD camera system 201 of the SVRS 200. The display unit 216 is a capacitive touch screen that receives one or more user inputs for controlling the operation of the UHD camera system 201 and displays the captured and communicated images of the surgical site associated with the received patient information with up to a 4K UHD resolution. The display unit 216 further comprises universal serial bus (USB) interfaces 242, 243, and 244. The USB interface 242 is used for connecting the display unit 216 to the UHD camera system 201 via the USB cable 212. The USB interface 243 is used for connecting the display unit 216 to the removable drive 218, for example, a USB flash drive, a storage hard disk drive, etc., for recording the captured and communicated images of the surgical site with the associated patient information and acquiring the pre-recorded images of the surgical site with the associated patient information. The embedded microcomputer 222 stores the captured and communicated images of the surgical site associated with the patient information in the removable drive 218 in real time. The display unit 216 also displays the pre-recorded images of the surgical site associated with the patient information and stored in the removable drive 218, on the tactile user interface 217. The USB interface 244 is used for connecting one or more input devices 302, for example, a foot switch, to the display unit 216 for allowing a user to control the camera parameters of the UHD camera system 201 and to control the capture, recording, displaying, and communication of the images of the surgical site.

The non-transitory computer readable storage medium disclosed herein stores computer program codes comprising instructions executable by at least one processor, for example, the microprocessor 225, for capturing, recording, and displaying images of a surgical site with up to a 4K ultrahigh definition (UHD) resolution in association with patient information in real time during a surgery. The computer program codes comprise a first computer program code for receiving patient information via the tactile user interface 217 of the display unit 216 and one or more user inputs for controlling the operation of the UHD camera system 201 via the tactile user interface 217 and/or via one or more of the input devices 302 operably connected to the display unit 216; a second computer program code for receiving images of the surgical site with up to 4K UHD resolution captured and communicated by the image sensor 220 of the UHD camera system 201 in real time on receiving one or more user inputs via the tactile user interface 217 of the display unit 216 and/or via one or more of the input devices 302; a third computer program code for associating the captured and communicated images of the surgical site with the received patient information in real time; and a fourth computer program code for displaying the captured and communicated images of the surgical site associated with the received patient information with up to a 4K UHD resolution on the tactile user interface 217 in real time.

In an embodiment, the computer program codes further comprise a fifth computer program code for recording the captured and communicated images of the surgical site with up to 4K ultrahigh definition (UHD) resolution and with the received patient information in a storage device, for example, the removable drive 218, in real time. In another embodiment, the computer program codes further comprise a sixth computer program code for securely storing the captured and communicated images of the surgical site with the received patient information on the external system 303 directly in real time. In another embodiment, the computer program codes further comprise a seventh computer program code for storing the captured and communicated images of the surgical site with the received patient information in a cloud computing environment over the network 301 in real time. In another embodiment, the computer program codes further comprise an eighth computer program code for controlling the capture, the recording, and the display of the captured and communicated images of the surgical site with up to a 4K UHD resolution and for controlling the capture and display of the pre-recorded images of the surgical site with up to a 4K UHD resolution on receiving one or more of the user inputs via the tactile user interface 217 of the display unit 216 and/or one or more of the input devices 302.

In another embodiment, the computer program codes further comprise a ninth computer program code for transmitting the captured and communicated images of the surgical site with up to a 4K ultrahigh definition (UHD) resolution and with the received patient information in real time to the client application 306 on the user device 305 via the network 301 for allowing viewing of the captured and communicated images of the surgical site with the received patient information on the user device 305 in real time. In another embodiment, the computer program codes further comprise a tenth computer program code for organizing the captured and communicated images of the surgical site with the received patient information in a file system. In another embodiment, the computer program codes further comprise an eleventh computer program code for controlling one or more of multiple camera parameters of the UHD camera system 201, on receiving one or more user inputs via the tactile user interface 217 of the display unit 216 and/or one or more input devices 302.

The computer program codes further comprise one or more additional computer program codes for performing additional steps that may be required and contemplated for capturing, communicating, and displaying images of a surgical site with up to a 4K ultrahigh definition (UHD) resolution in association with patient information in real time during a surgery. In an embodiment, a single piece of computer program code comprising computer executable instructions performs one or more steps of the method disclosed herein for capturing, communicating, and displaying images of a surgical site with up to a 4K UHD resolution in association with patient information in real time during a surgery. The computer program codes comprising computer executable instructions are embodied on the non-transitory computer readable storage medium. The microprocessor 225 of the embedded microcomputer 222 retrieves these computer executable instructions and executes them. When the computer executable instructions are executed by the microprocessor 225, the computer executable instructions cause the microprocessor 225 to perform the steps of the method for capturing, communicating, and displaying images of a surgical site with up to a 4K UHD resolution in association with patient information in real time during a surgery.

Figure 4:
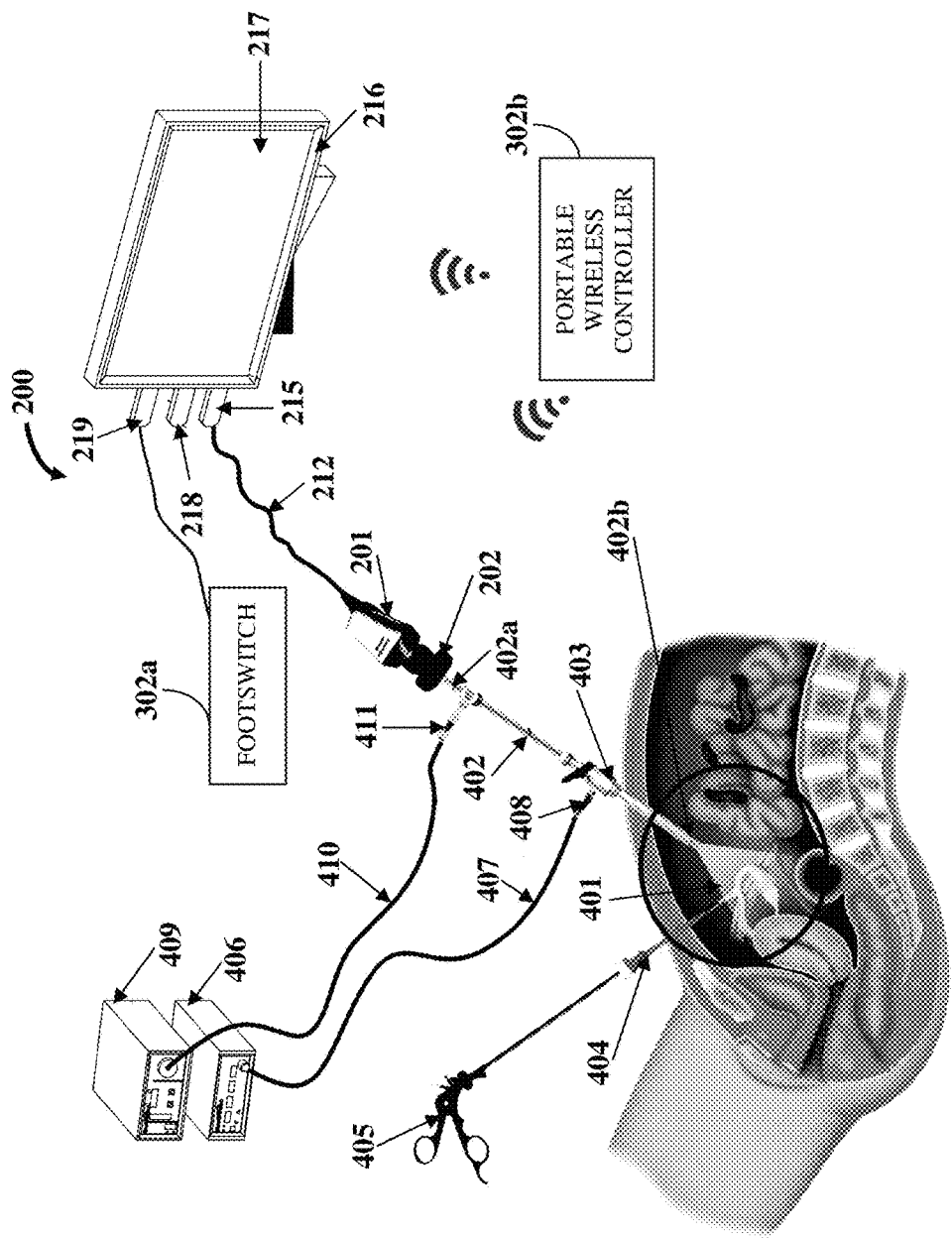
FIG. 4 exemplarily illustrates the surgical visualization and recording system used for capturing, communicating, and displaying images of a surgical site with up to an ultrahigh definition resolution in association with patient information in real time during a laparoscopy.

FIG. 4 exemplarily illustrates the surgical visualization and recording system (SVRS) 200 used for capturing, communicating, and displaying images of a surgical site 401 with up to a 4K ultrahigh definition (UHD) resolution in association with patient information in real time during a laparoscopy. The SVRS 200 facilitates the performance of the laparoscopy by a surgeon. The surgeon connects the ultrahigh definition (UHD) camera system 201 of the SVRS 200 to a proximal end 402a of a surgical scope device, for example, a laparoscope 402. The laparoscope 402 is an elongated, thin fiber optic rigid instrument with a high intensity light and a UHD resolution camera positioned at the proximal end 402a of the laparoscope 402. The surgeon also connects the universal serial bus (USB) cable 212 that is operably coupled to the UHD camera system 201, to the display unit 216 of the SVRS 200 using the USB interface connector 215. The surgeon makes one or more small incisions of, for example, about 0.5 centimeters to about 1.5 centimeters in the skin of the patient. The surgeon inserts trocars 403 and 404 with diameters of, for example, about 5 millimeters (mm) and about 10 mm respectively, into the abdominal wall of the patient through the incisions to reach the surgical site 401, for example, the peritoneal cavity. The trocars 403 and 404 are medical devices, each comprising an obturator that obstructs the incision, a hollow tube or a cannula, and a seal. The trocars 403 and 404 function as portals for inserting instruments, for example, a grasper 405, a scissor, a stapler, the laparoscope 402, etc. The surgeon connects an insufflator 406 to the trocar 403 by an insufflator tube 407 via an insufflator adapter 408. The insufflator 406 provides a gas, for example, carbon dioxide, through the insufflator tube 407 to inflate the surgical site 401 for performing the laparoscopy. The surgeon inserts the laparoscope 402 through the trocar 403. The surgeon connects a light cable 410 extending from a light source 409 to the laparoscope 402 via a light adapter 411. The light source 409 provides light to the laparoscope 402 through the light cable 410. The light source 409, for example, is a light emitting diode (LED) light source. The light cable 410 is, for example, a fiber optic cable, a liquid crystal gel cable, etc.

The light, from the light source 409, in the light cable 410 traverses the light cable 410 by reflection from the interior walls of the light cable 410 and illuminates the surgical site 401. The surgical site 401 reflects the light that is focused on the surgical site 401. An optical lens (not shown) positioned at a distal end 402b of the laparoscope 402 receives the light reflected from the surgical site 401. The optical lens on the laparoscope 402 focuses the reflected light from the surgical site 401 to a fiber optic cable in the laparoscope 402. The reflected light from the surgical site 401 traverses the fiber optic cable in the laparoscope 402 and reaches the optical component 203 of the ultrahigh definition (UHD) camera system 201 exemplarily illustrated in the FIGS. 2-3. The reflected light from the surgical site 401 on the optical component 203 is directed to the image sensor 220 of the UHD camera system 201 exemplarily illustrated in the FIGS. 2-3. The image sensor 220 receives the reflected light and captures images of the surgical site 401. The image sensor 220 conveys the information that constitutes the captured images to the embedded microcomputer 222 of the display unit 216 as disclosed in the detailed description of FIGS. 1-3. The image sensor 220 communicates the captured images with up to a 4K UHD resolution to the embedded microcomputer 222 of the display unit 216 via the universal serial bus (USB) cable 212 and the USB interface connector 215. The surgeon inserts the grasper 405 through the trocar 404. The grasper 405 is a device for grasping and holding a tissue in the surgical site 401.

The surgeon activates the surgical visualization and recording system (SVRS) 200. The embedded microcomputer 222 of the display unit 216 renders a start screen on the tactile user interface 217 of the display unit 216 and determines whether the ultrahigh definition (UHD) camera system 201 and the removable drive 218 are connected to the display unit 216. The embedded microcomputer 222 renders a run screen on the tactile user interface 217 of the display unit 216 and activates one or more buttons on the run screen based on the connection of the UHD camera system 201 and/or the connection of the removable drive 218 to the display unit 216. The surgeon clicks a button corresponding to camera settings on the tactile user interface 217 to set the camera parameters. The embedded microcomputer 222 renders a camera settings screen on the tactile user interface 217 to allow the surgeon to set the camera parameters. The surgeon exits the camera settings screen and returns to the run screen. The surgeon clicks a button corresponding to patient information on the run screen. The embedded microcomputer 222 renders a patient information screen on the tactile user interface 217. The surgeon enters patient information on the tactile user interface 217, views the patient's medical history, exits the patient information screen, and returns to the run screen.

The surgeon then clicks a button corresponding to capturing and recording a single image or a button for capturing and recording multiple images to be displayed at a defined rate on the tactile user interface 217. The embedded microcomputer 222 renders a video recording and image capture screen on the tactile user interface 217 of the display unit 216. The image sensor 220 of the ultrahigh definition (UHD) camera system 201 captures images of the surgical site 401 with up to a 4K UHD resolution and communicates the captured images of the surgical site 401 to the embedded microcomputer 222 of the display unit 216 in real time. The embedded microcomputer 222 associates the captured and communicated images of the surgical site 401 with the patient information in real time. In an embodiment, the embedded microcomputer 222 records the captured and communicated images of the surgical site 401 with up to a 4K UHD resolution and with the patient information in the removable drive 218 in real time. The display unit 216 displays the captured and communicated images of the surgical site 401 associated with the patient information with up to a 4K UHD resolution on the tactile user interface 217 in real time. The surgeon can visualize the captured and communicated images of the surgical site 401 in real time and perform the laparoscopy with ease and complete concentration.

The light source 409 connected to the laparoscope 402 aids the surgeon performing the laparoscopy by illuminating the surgical site 401. After completing the laparoscopy, the surgeon may exit the video recording and image capture screen and return to the run screen on the tactile user interface 217 of the display unit 216. If the surgeon wishes to review the captured and communicated images of the surgical site 401 recorded in the removable drive 218, the surgeon clicks a button for viewing the pre-recorded images on the tactile user interface 217 of the display unit 216. The embedded microcomputer 222 renders a media viewer screen on the tactile user interface 217 to allow the surgeon to view the captured and communicated images. The surgeon may then exit the media viewer screen and return to the run screen on the tactile user interface 217. The surgeon may then switch the surgical visualization and recording system 200 off by clicking a power off button on the tactile user interface 217. The embedded microcomputer 222 closes the run screen and initiates a shutdown routine. The surgeon may then disconnect the removable drive 218 with the directly recorded captured and communicated images of the surgical site 401 and transfer the recorded captured and communicated images of the surgical site 401 to a secure hospital system to avoid mishandling and manipulation of the patient information along with the recorded images of the surgical site 401 by unauthorized staff and to maintain confidentiality of the patient information under the Health Insurance Portability and Accountability Act (HIPAA).

In an embodiment, a foot switch 302a is connected to the display unit 216 through a universal serial bus (USB) interface connector 219. The surgeon may use the foot switch 302a to control the capture, recording, and display of the captured and communicated images of the surgical site 401 and/or the display of the pre-recorded images of the surgical site 401 on the display unit 216. In another embodiment, the surgeon's technician may use a portable wireless controller 302b that wirelessly communicates with the display unit 216, to control the capture, recording, and display of the captured and communicated images of the surgical site 401 and/or the display of the pre-recorded images of the surgical site 401 on the display unit 216.

Figure 5:
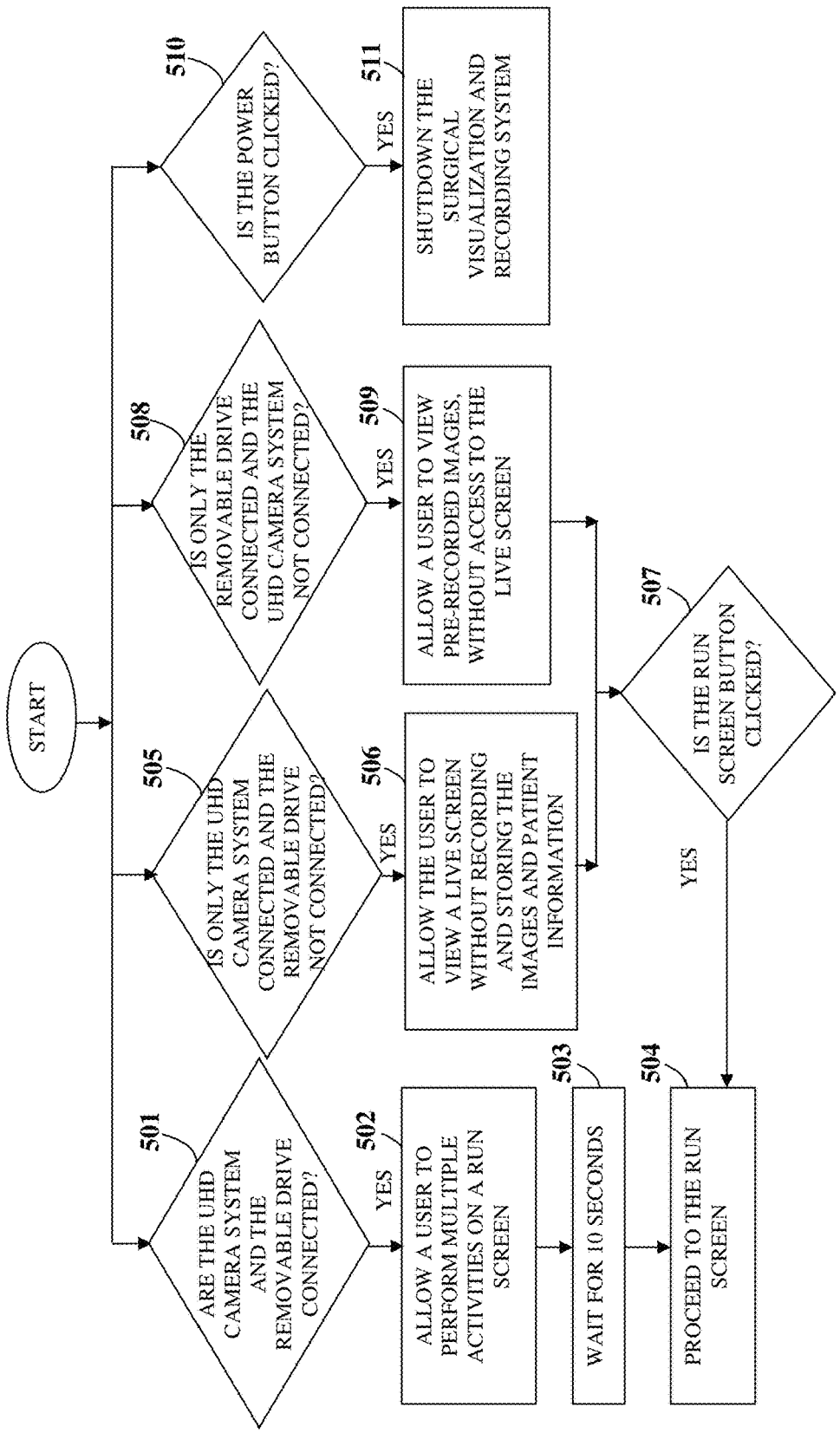
FIG. 5 exemplarily illustrates a flowchart comprising the steps performed by an embedded microcomputer of a display unit of the surgical visualization and recording system based on user inputs received on a start screen rendered on a tactile user interface of the display unit.

FIG. 5 exemplarily illustrates a flowchart comprising the steps performed by the embedded microcomputer 222 of the display unit 216 of the surgical visualization and recording system (SVRS) 200 exemplarily illustrated in FIG. 3, based on user inputs received on a start screen rendered on the tactile user interface 217 of the display unit 216 exemplarily illustrated in FIG. 2. The start screen comprises a power button and a run screen button. The embedded microcomputer 222 determines 501 whether the ultrahigh definition (UHD) camera system 201 and the removable drive 218 exemplarily illustrated in FIGS. 2-3, are connected to the display unit 216 through the embedded microcomputer 222. If the UHD camera system 201 and the removable drive 218 are connected to the display unit 216 through the embedded microcomputer 222, the embedded microcomputer 222 allows 502 a user, for example, a surgeon to perform multiple activities on the run screen such as controlling the capture, recording, storing, and displaying of images of the surgical site during a surgery in real time, viewing the pre-recorded images of the surgical site in the removable drive 218, etc. The embedded microcomputer 222 waits 503 for about 10 seconds and proceeds 504 to the run screen. The embedded microcomputer 222 also determines 505 whether the UHD camera system 201 is connected to the display unit 216 and whether the removable drive 218 is not connected to the display unit 216 through the embedded microcomputer 222. If the UHD camera system 201 is connected to the display unit 216 and the removable drive 218 is not connected to the display unit 216 through the embedded microcomputer 222, the embedded microcomputer 222 allows 506 the user to view a live screen rendered on the tactile user interface 217, displaying the captured and communicated images of the surgical site in real time, without recording and storing the captured and communicated images of the surgical site and patient information.

The embedded microcomputer 222 also determines 508 whether the removable drive 218 is connected to the display unit 216 through the embedded microcomputer 222 and whether the ultrahigh definition (UHD) camera system 201 is not connected to the display unit 216. If the removable drive 218 is connected to the display unit 216 through the embedded microcomputer 222 and the UHD camera system 201 is not connected to the display unit 216, the embedded microcomputer 222 allows 509 the user to view pre-recorded images, for example, pre-recorded still images and videos stored in the removable drive 218 on the display unit 216, without providing access to the live screen on the tactile user interface 217 of the display unit 216 for viewing the captured and communicated images of the surgical site in real time. The embedded microcomputer 222 determines 507 whether the user clicked the run screen button on the tactile user interface 217. If the user clicked the run screen button, the embedded microcomputer 222 proceeds 504 to the run screen. The embedded microcomputer 222 also determines 510 whether the user clicked on the power button of the start screen. If the user clicked on the power button, the embedded microcomputer 222 shuts down 511 the surgical visualization and recording system 200 by initiating a shutdown routine.

Figure 6A:
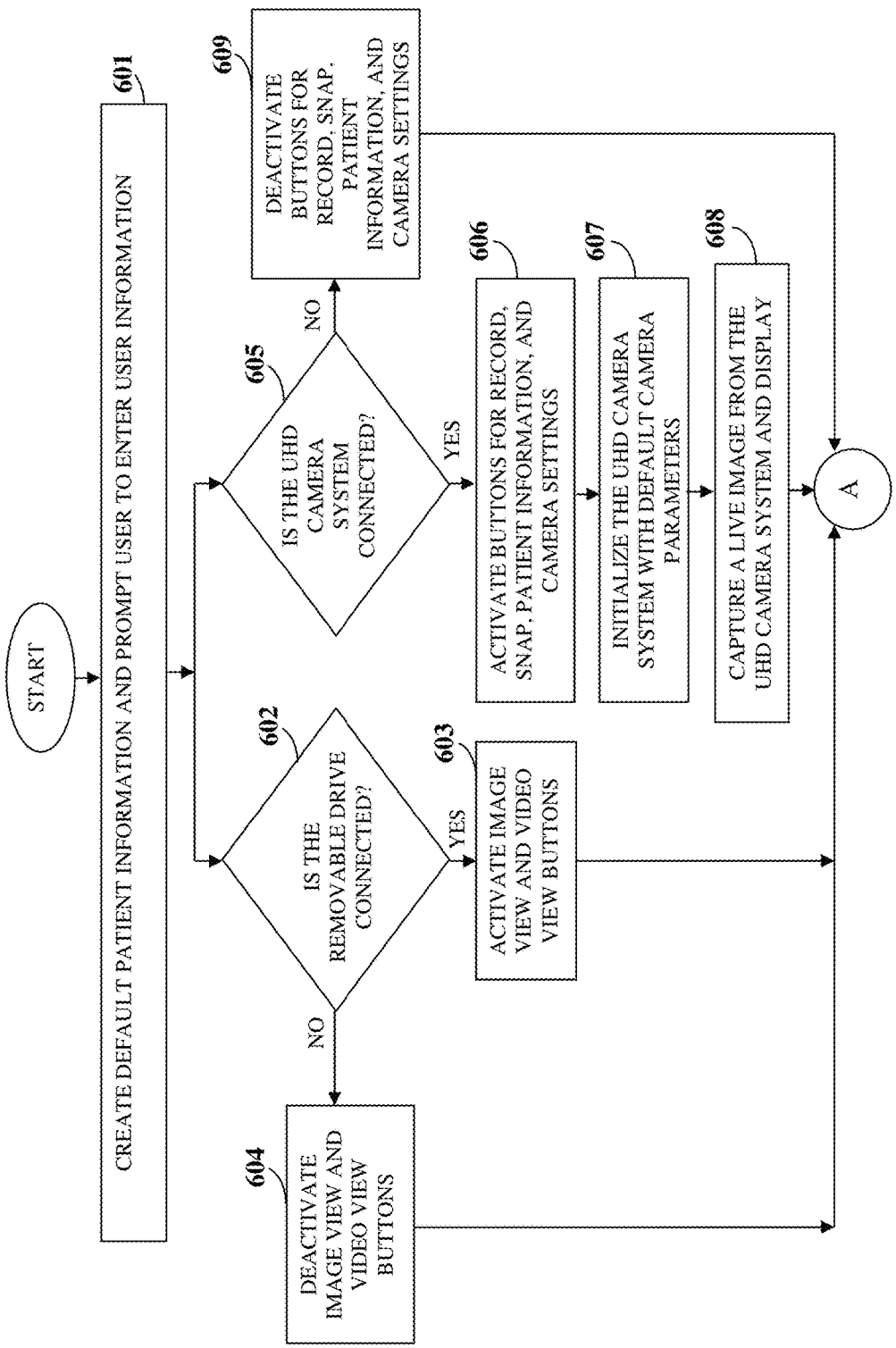
FIGS. 6A-6B exemplarily illustrate a flowchart comprising the steps performed by the embedded microcomputer of the display unit based on user inputs received on a run screen rendered on the tactile user interface of the display unit.
Figure 6B:
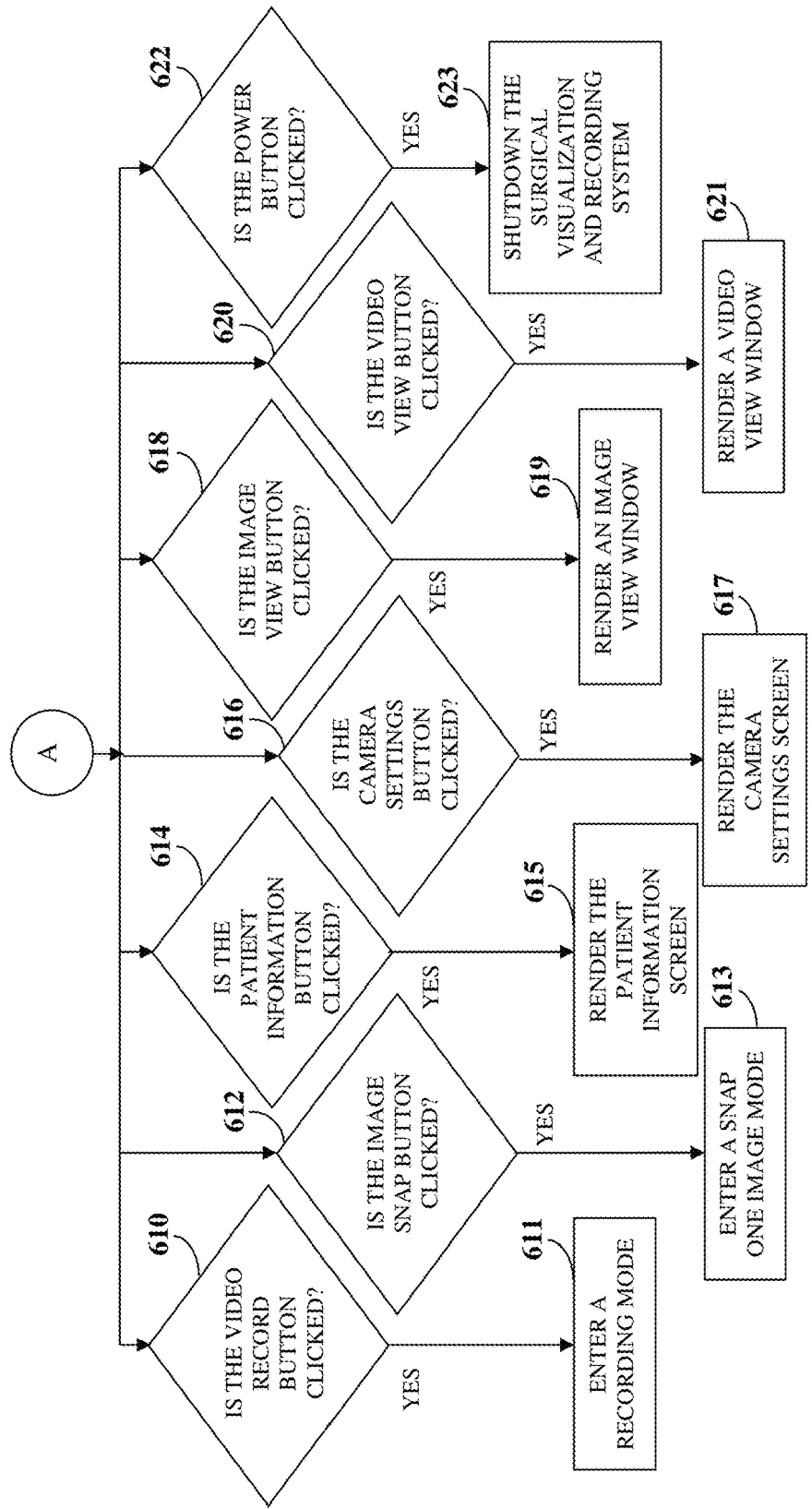

FIGS. 6A-6B exemplarily illustrate a flowchart comprising the steps performed by the embedded microcomputer 222 of the display unit 216 exemplarily illustrated in FIG. 3, based on user inputs received on the run screen rendered on the tactile user interface 217 of the display unit 216 exemplarily illustrated in FIG. 2. The embedded microcomputer 222 creates 601 and displays default patient information, for example, patient identifier, patient name, etc., on the run screen, and prompts a user, for example, a surgeon, to enter user information, for example, surgeon name, type of surgery, description of the surgery, etc. The embedded microcomputer 222 determines 602 whether the removable drive 218 exemplarily illustrated in FIG. 2, is connected to the display unit 216 through the embedded microcomputer 222. If the removable drive 218 is connected to the display unit 216 through the embedded microcomputer 222, the embedded microcomputer 222 activates 603 an image view button and a video view button on the run screen. The embedded microcomputer 222 determines 618 whether the image view button is clicked. If the image view button is clicked, the embedded microcomputer 222 renders 619 an image view window on the tactile user interface 217 of the display unit 216. The embedded microcomputer 222 determines 620 whether the video view button is clicked. If the video view button is clicked, the embedded microcomputer 222 renders 621 a video view window on the tactile user interface 217. If the removable drive 218 is not connected to the display unit 216 through the embedded microcomputer 222, the embedded microcomputer 222 deactivates 604 the image view button and the video view button on the run screen.

The embedded microcomputer 222 determines 605 whether the ultrahigh definition (UHD) camera system 201 exemplarily illustrated in FIGS. 2-3, is connected to the display unit 216. If the UHD camera system 201 is connected to the display unit 216, the embedded microcomputer 222 activates 606 buttons for video record, image snap, patient information, and camera settings. The embedded microcomputer 222 initializes 607 the UHD camera system 201 with default camera parameters. The image sensor 220 of the UHD camera system 201 exemplarily illustrated in FIG. 3, captures 608 a live image of a surgical site with up to a 4K UHD resolution and communicates the live image of the surgical site to the embedded microcomputer 222 of the display unit 216. The display unit 216 displays the live image on the tactile user interface 217. The embedded microcomputer 222 determines 610 whether a video record button is clicked on the run screen. If the video record button is clicked on the run screen, the embedded microcomputer 222 enters 611 a recording mode for recording the live image. The embedded microcomputer 222 determines 612 whether an image snap button is clicked on the run screen. If the image snap button is clicked on the run screen, the embedded microcomputer 222 enters 613 a snap one image mode for capturing one image of the surgical site. The embedded microcomputer 222 determines 614 whether a patient information button is clicked on the run screen. If the patient information button is clicked on the run screen, the embedded microcomputer 222 renders 615 the patient information screen on the tactile user interface 217 of the display unit 216. The embedded microcomputer 222 determines 616 whether a camera settings button is clicked on the run screen. If the camera settings button is clicked on the run screen, the embedded microcomputer 222 renders 617 the camera settings screen on the tactile user interface 217. If the UHD camera system 201 is not connected to the display unit 216, the embedded microcomputer 222 deactivates 609 the buttons for video record, image snap, patient information, and camera settings. The embedded microcomputer 222 determines 622 whether the power button is clicked on the run screen. If the power button is clicked on the run screen, the embedded microcomputer 222 shuts down 623 the surgical visualization and recording system 200 by initiating the shutdown routine.

Figure 7A:
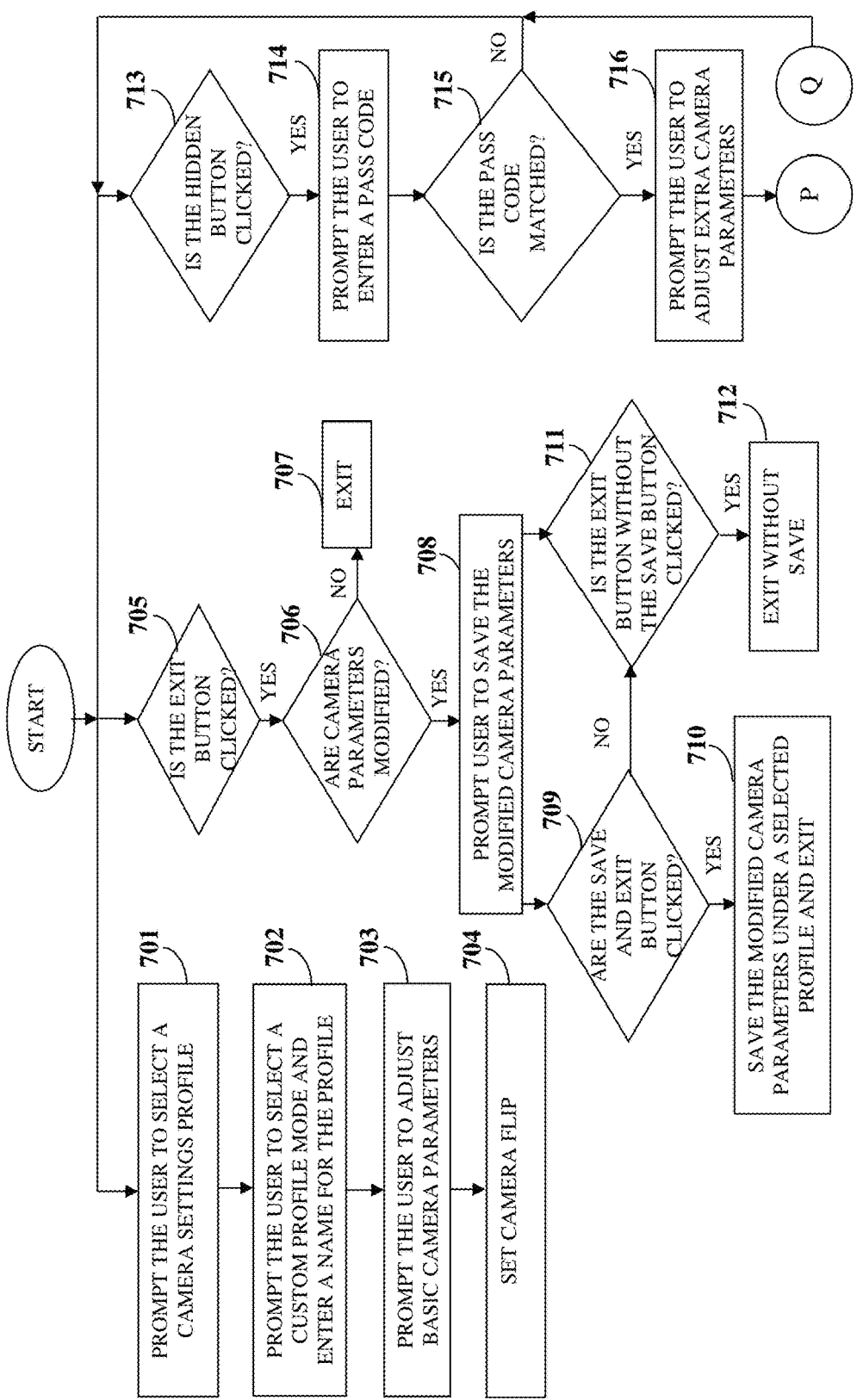
FIGS. 7A-7B exemplarily illustrate a flowchart comprising the steps performed by the embedded microcomputer of the display unit based on user inputs received on a camera settings screen rendered on the tactile user interface of the display unit.
Figure 7B:
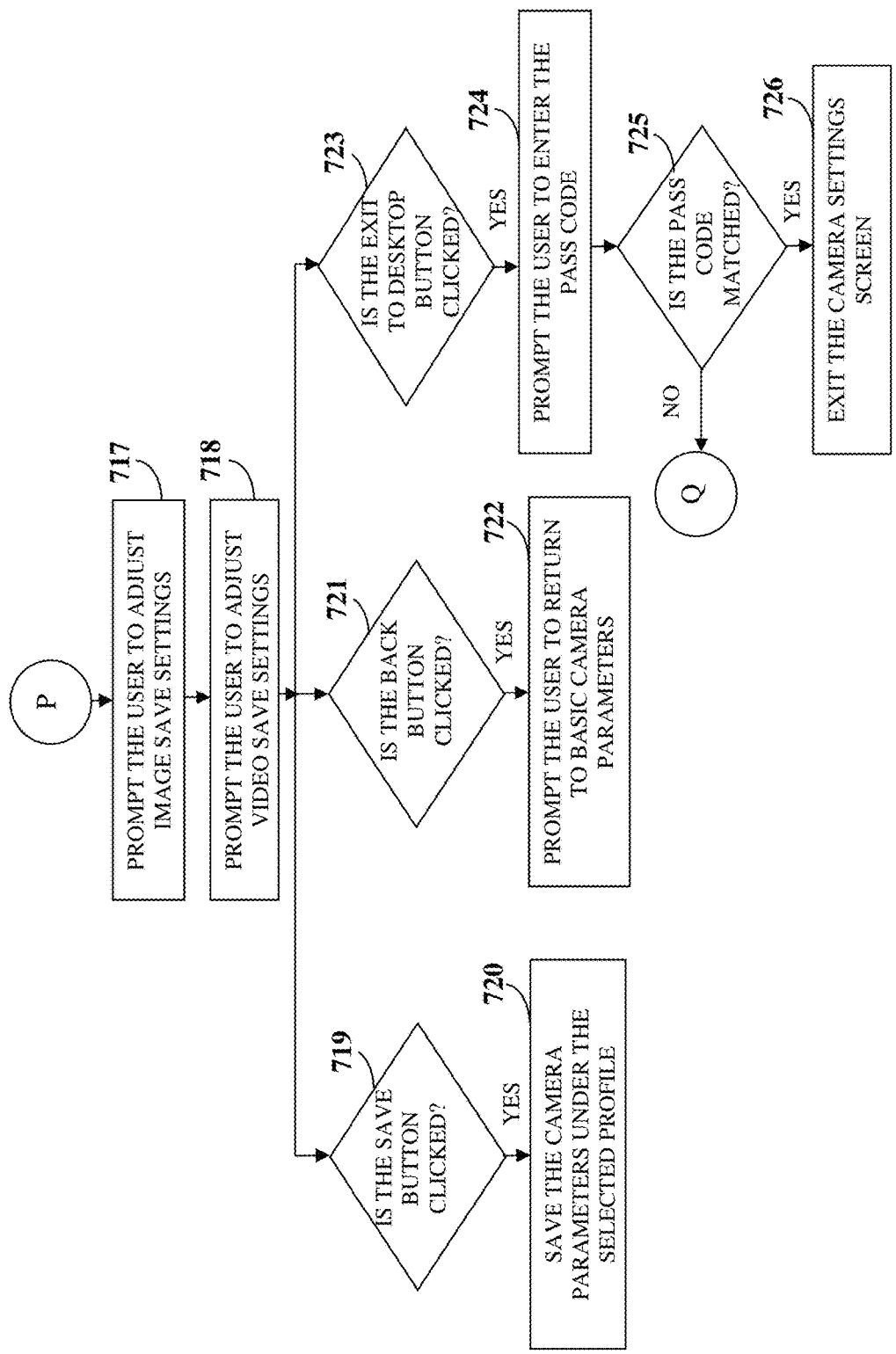

FIGS. 7A-7B exemplarily illustrate a flowchart comprising the steps performed by the embedded microcomputer 222 of the display unit 216 exemplarily illustrated in FIG. 3, based on user inputs received on the camera settings screen rendered on the tactile user interface 217 of the display unit 216 exemplarily illustrated in FIG. 2. The camera settings screen comprises, for example, an exit button, a hidden button, a save button, a back button, and an exit to desktop button. The embedded microcomputer 222 provides one or more camera settings profiles with predefined values, where a user cannot change typical camera parameters. The camera parameters comprise, for example, brightness, sharpness, contrast, gamma, saturation, auto white balance, resolution, gain, exposure, frame rate, etc. The embedded microcomputer 222 sets a default standard camera settings profile. The embedded microcomputer 222 prompts 701 the user to select a camera settings profile. The embedded microcomputer 222 prompts 702 the user to select a custom profile mode and enter a name for a custom profile. The embedded microcomputer 222 then prompts 703 the user to adjust the values of the basic camera parameters, for example, brightness, contrast, sharpness, auto balance, gain, exposure, frame rate, etc. The embedded microcomputer 222 sets 704 a camera flip that provides an option to flip the image.

The embedded microcomputer 222 determines 705 whether the exit button is clicked on the camera settings screen. If the exit button is clicked on the camera settings screen, the embedded microcomputer 222 determines 706 whether the camera parameters are modified. If the camera parameters are not modified, the embedded microcomputer 222 exits 707 the camera settings screen. If the camera parameters are modified, the embedded microcomputer 222 prompts 708 the user to save the modified camera parameters. The embedded microcomputer 222 provides a save and exit button, and an exit without save button on the camera settings screen. The embedded microcomputer 222 determines 709 whether the save and exit button is clicked on the camera settings screen. If the save and exit button is clicked on the camera settings screen, the embedded microcomputer 222 saves 710 the modified camera parameters under the selected camera settings profile and exits the camera settings screen. The embedded microcomputer 222 determines 711 whether the exit without save button is clicked on the camera settings screen. If the exit without save button is clicked on the camera settings screen, the embedded microcomputer 222 exits 712 the camera settings screen without saving the modified camera parameters.

The embedded microcomputer 222 also determines 713 whether the hidden button is clicked on the camera settings screen. If the hidden button is clicked on the camera settings screen, the embedded microcomputer 222 prompts 714 the user to enter a pass code or a password. The embedded microcomputer 222 receives the entered pass code and compares 715 the received pass code with a pass code stored in the internal database 239 and/or the storage device 234 exemplarily illustrated in FIG. 3. If the embedded microcomputer 222 determines a match between the received pass code and the pass code stored in the internal database 239 and/or the storage device 234, the embedded microcomputer 222 prompts 716 the user to adjust extra camera parameters and receives the adjusted extra camera parameters. The extra parameters comprise, for example, saturation, gamma, calibrate, white balance, set exposure to auto or manual, image save and video settings for resolution and type of format, etc. If the embedded microcomputer 222 determines a mismatch in the passcodes, the embedded microcomputer 222 performs the steps 701, 705, and 713 disclosed above.

The embedded microcomputer 222 prompts 717 the user to adjust the image save settings for resolution and type of the format. The embedded microcomputer 222 prompts 718 the user to adjust the video save settings for resolution and type of the format. The embedded microcomputer 222 receives and stores the adjusted image save settings and the adjusted video save settings in the internal database 239 and/or the storage device 234. The embedded microcomputer 222 determines 719 whether the save button is clicked on the camera settings screen. If the save button is clicked on the camera settings screen, the embedded microcomputer 222 saves 720 the camera parameters under the selected camera settings profile. The embedded microcomputer 222 then exits the extra parameters mode. The embedded microcomputer 222 determines 721 whether the back button is clicked on the camera settings screen. If the back button is clicked on the camera settings screen, the embedded microcomputer 222 prompts 722 the user to return to the basic camera parameters. The embedded microcomputer 222 determines 723 whether the exit to desktop button is clicked on the camera settings screen. If the exit to desktop button is clicked on the camera settings screen, the embedded microcomputer 222 prompts 724 the user to enter the pass code. The embedded microcomputer 222 receives the entered pass code and compares 725 the received pass code with the pass code stored in the internal database 239 and/or the storage device 234. If the embedded microcomputer 222 determines a match between the received pass code and the stored pass code, the embedded microcomputer 222 exits 726 the camera settings screen. If the embedded microcomputer 222 determines a mismatch in the passcodes, the embedded microcomputer 222 performs the steps 701, 705, and 713 disclosed above.

Figure 8A:
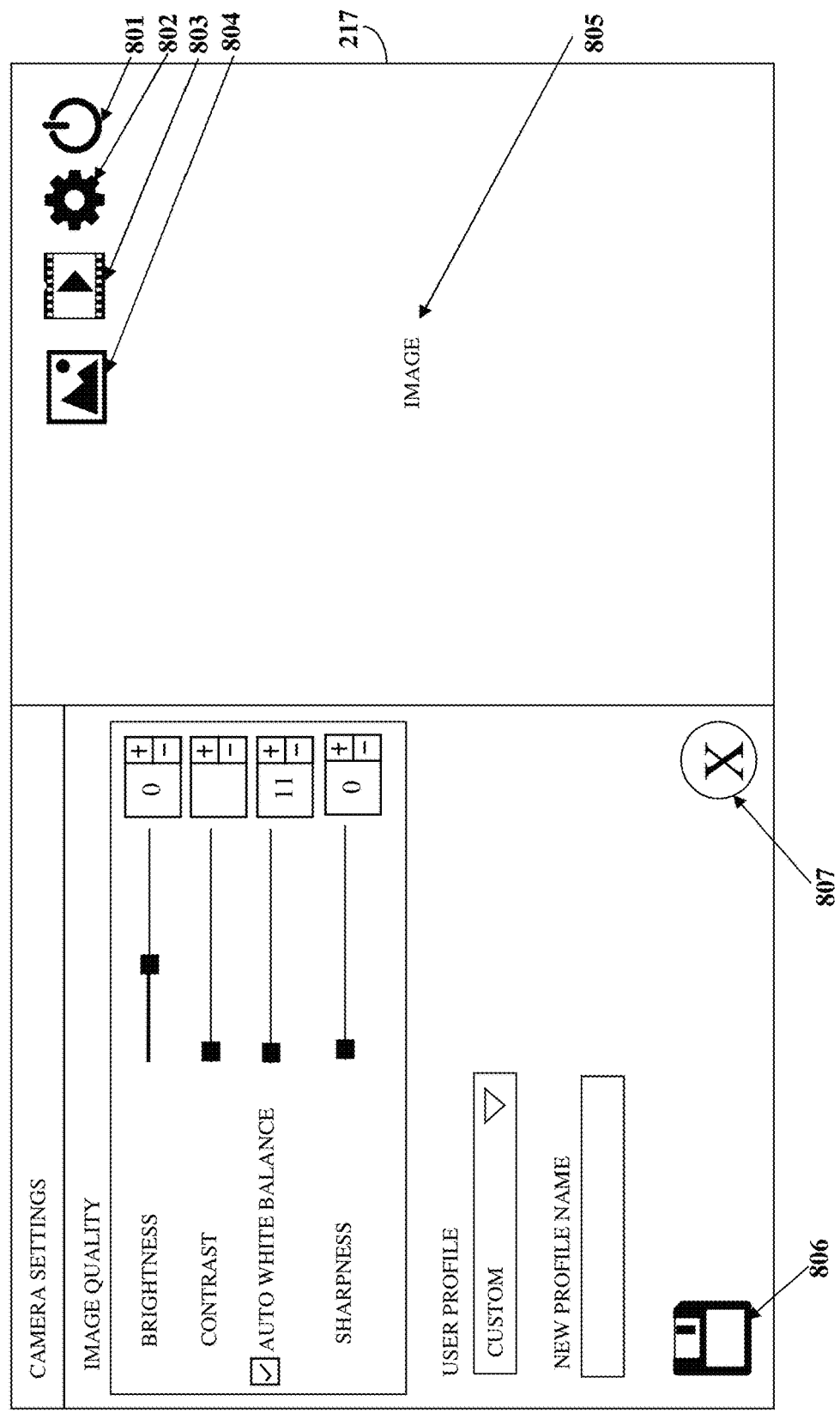
FIGS. 8A-8B exemplarily illustrate screenshots of the tactile user interface of the display unit, displaying the camera settings screen for modifying camera parameters of an ultrahigh definition camera system of the surgical visualization and recording system.
Figure 8B:
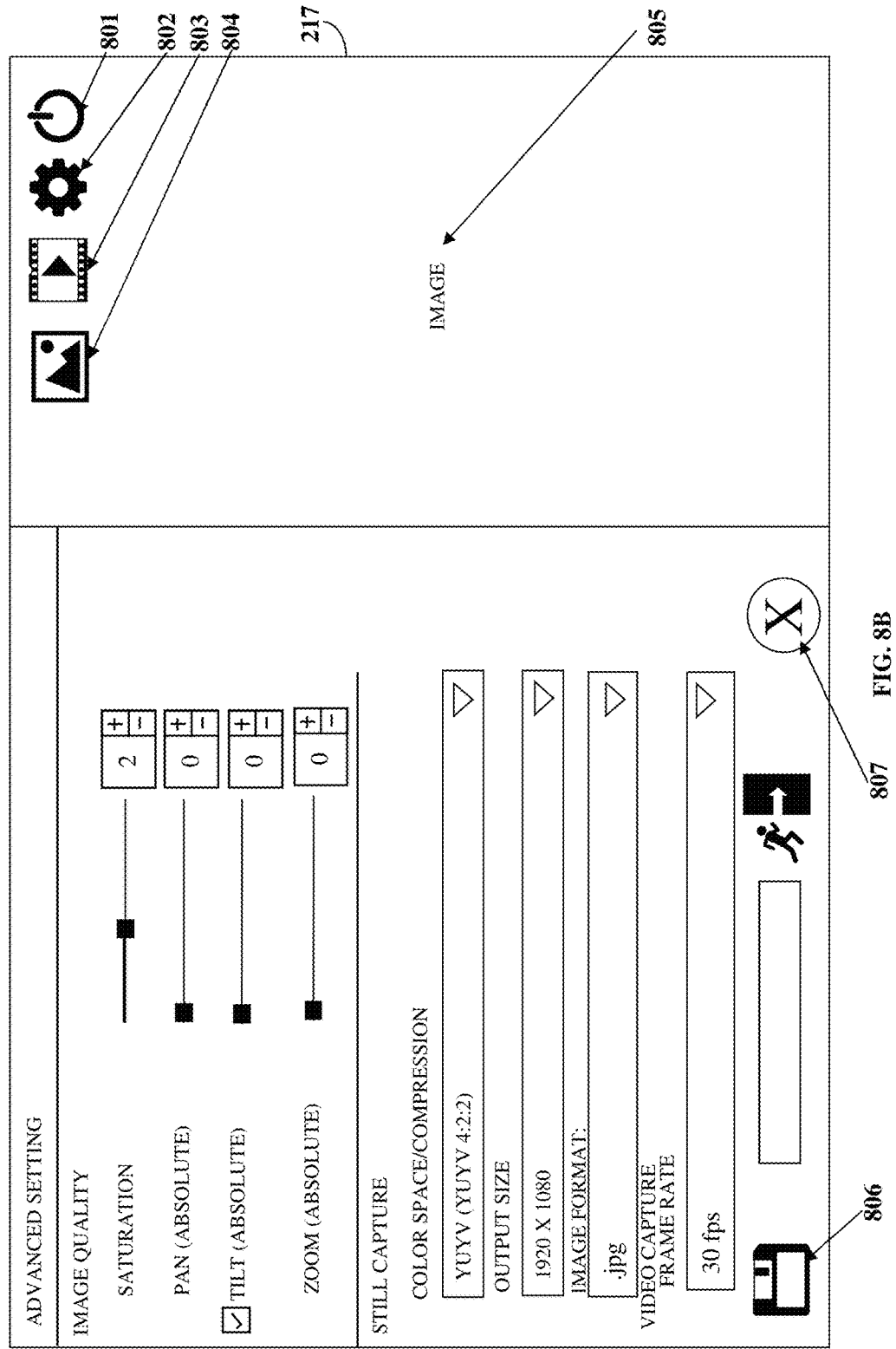

FIGS. 8A-8B exemplarily illustrate screenshots of the tactile user interface 217 of the display unit 216 exemplarily illustrated in FIG. 2, displaying the camera settings screen for modifying camera parameters of the ultrahigh definition (UHD) camera system 201 of the surgical visualization and recording system (SVRS) 200 exemplarily illustrated in FIG. 2. The tactile user interface 217 displays buttons, for example, a power off button 801, a camera settings button 802, a video record button 803, and an image snap button 804. When a user clicks the camera settings button 802, the tactile user interface 217 displays the camera settings screen exemplarily illustrated in FIG. 8A, for modifying basic camera parameters of the UHD camera system 201. The embedded microcomputer 222 prompts a user to select a camera settings profile and enter a name for the selected camera settings profile as disclosed in the detailed description of FIGS. 7A-7B. The camera settings screen displays a dropdown menu for providing options of the camera settings profile to a user. The user selects the camera settings profile from the dropdown menu. When the user selects a custom profile, the embedded microcomputer 222 prompts the user to enter a name for the custom profile. The user enters the name of the custom profile in a text box provided on the camera settings screen for receiving the name for the custom profile. The camera settings screen displays value adjustment scales and value adjustment boxes for adjusting the basic camera parameters. The user adjusts the values of basic camera parameters, for example, brightness, contrast, auto white balance, and sharpness using a value adjustment scale or a value adjustment box corresponding to each basic camera parameter. As exemplarily illustrated in FIG. 8A, the camera settings screen displays a checkbox for setting auto white balance. When the user checks the checkbox, the embedded microcomputer 222 determines the check and activates the value adjustment scale corresponding to the auto white balance parameter. The camera settings screen displays a save button 806 and an exit button 807. The user can save the selected camera settings profile with the name of the camera settings profile and the values of the basic camera parameters using the save button 806 as disclosed in the detailed description of FIGS. 7A-7B. The user can exit the camera settings screen using the exit button 807 as disclosed in the detailed description of FIGS. 7A-7B.

When a user clicks the camera settings button 802, the tactile user interface 217 displays a camera settings screen exemplarily illustrated in FIG. 8B, for adjusting extra camera parameters of the ultrahigh definition (UHD) camera system 201. The camera settings screen displays value adjustment scales and value adjustment boxes for adjusting the extra camera parameters. The embedded microcomputer 222 prompts a user to adjust the extra camera parameters as disclosed in the detailed description of FIGS. 7A-7B. The user adjusts the values of extra camera parameters, for example, saturation, pan, tilt, zoom, gamma, etc., using a value adjustment scale or a value adjustment box corresponding to each extra camera parameter. The camera settings screen displays dropdown menus for providing a list of options to the user for selecting the values of the extra camera parameters, for example, as color space or compression, output size, image format, etc., for image capture, and extra camera parameters, for example, frame rate, color space or compression, etc., for video capture. The user may select, for example, YUYV (YUYV 4:2:2) for the color space or compression, 1920×1080 as the output size, and a joint photographic experts group (jpeg) file extension such as ".jpg" as the image format for the image capture from the dropdown menus. The user may also select, for example, 30 frames per second (fps) as the frame rate and YUYV (YUYV 4:2:2) for the color space or compression for the video capture from the dropdown menus. The tactile user interface 217 displays a live image 805 adjacent to the camera settings screen as exemplarily illustrated in FIGS. 8A-8B, and allows the user to modify the basic camera parameters and extra camera parameters while viewing the live image 805. When the live image 805 is displayed on the tactile user interface 217 with up to a 4K UHD resolution, the user may click on the image snap button 804 to capture an image of a surgical site being streamed or click on the video record button 803 to record a video of the surgical site being streamed. The user may click on the power off button 801 to power off the surgical visualization and recording system 200.

Figure 9A:
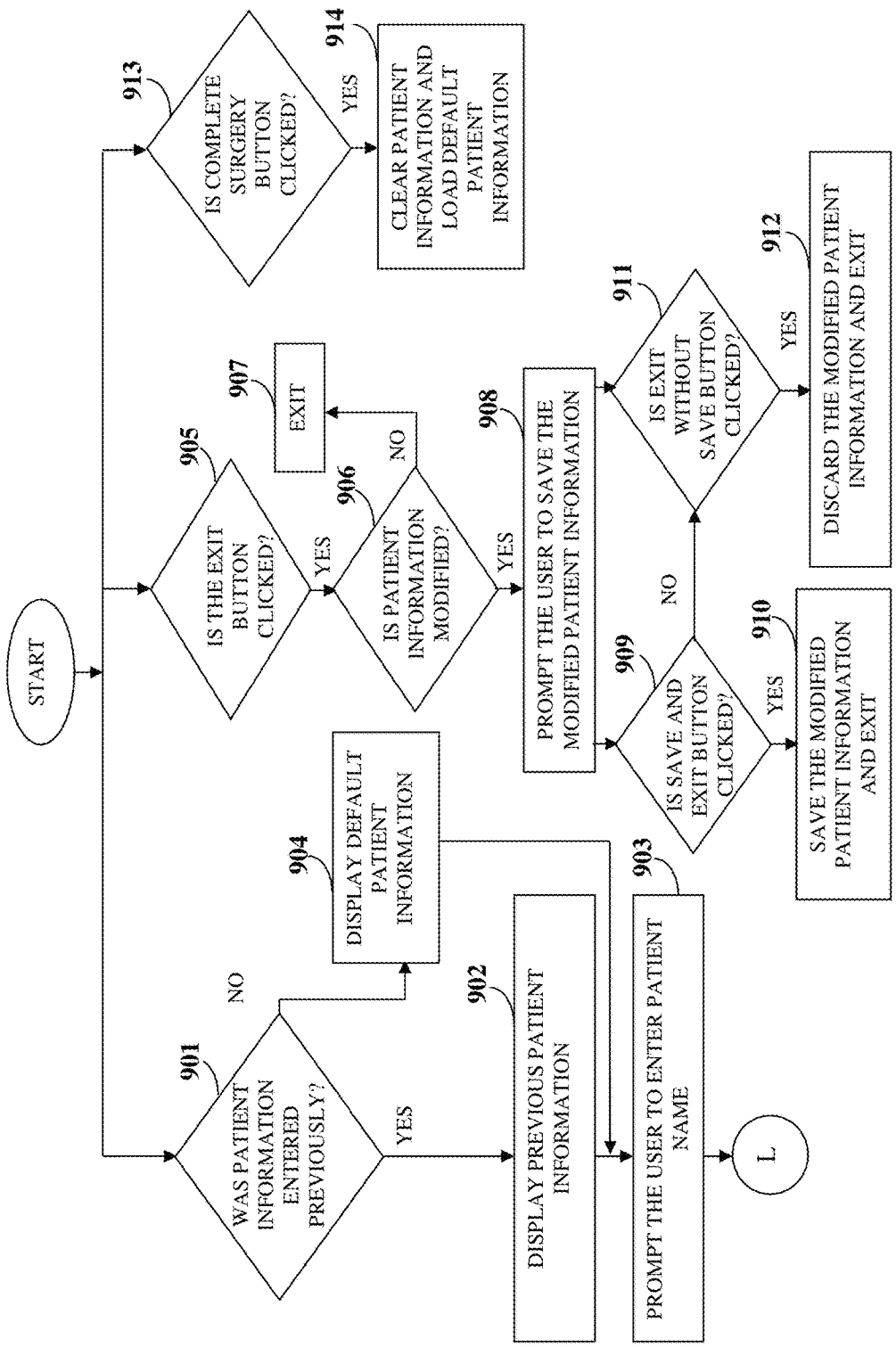
FIGS. 9A-9B exemplarily illustrate a flowchart comprising the steps performed by the embedded microcomputer of the display unit based on user inputs received on a patient information screen rendered on the tactile user interface of the display unit.
Figure 9B:
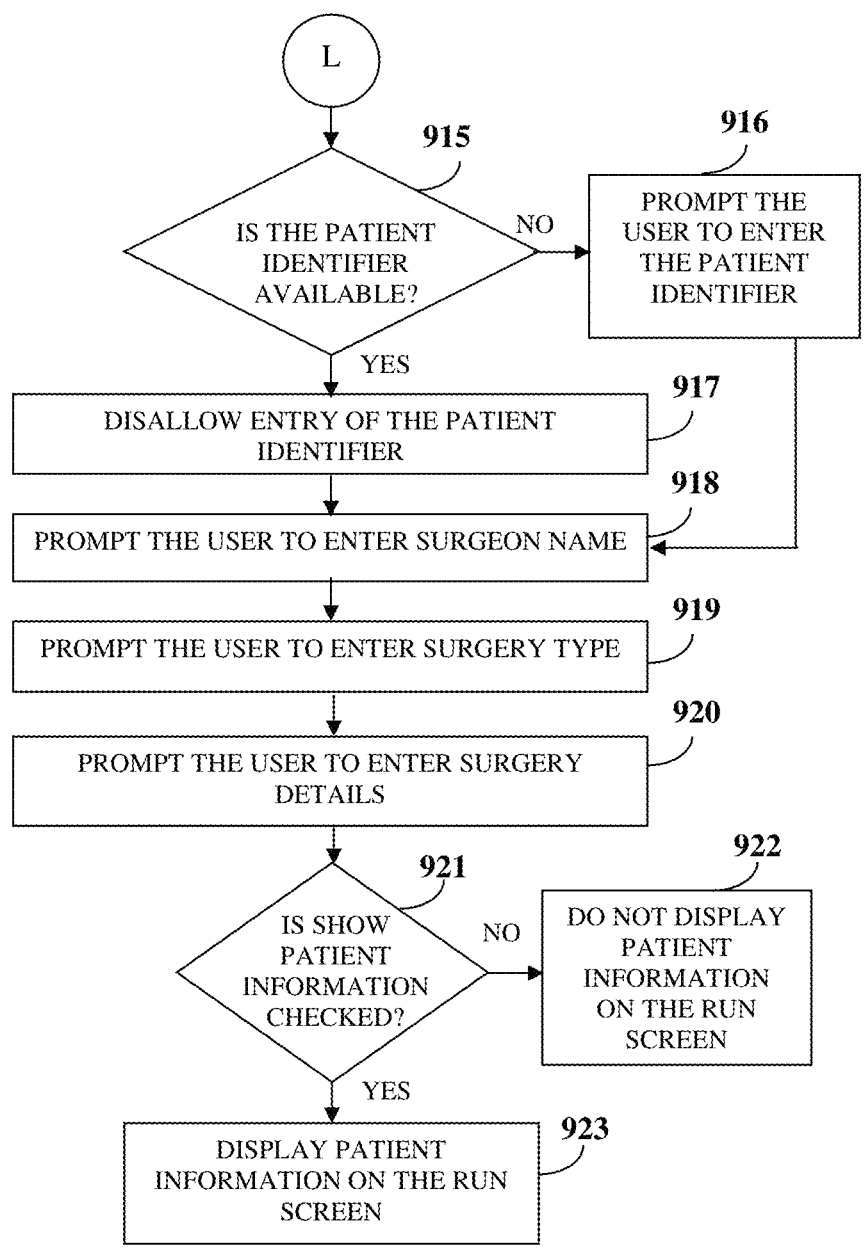

FIGS. 9A-9B exemplarily illustrate a flowchart comprising the steps performed by the embedded microcomputer 222 of the display unit 216 exemplarily illustrated in FIG. 3, based on user inputs received on the patient information screen rendered on the tactile user interface 217 of the display unit 216 exemplarily illustrated in FIG. 2. The patient information screen comprises, for example, an exit button, a save and exit button, a discard changes and exit button, a complete surgery button, and a show patient information checkbox. The embedded microcomputer 222 determines 901 whether patient information was entered previously. If the patient information was entered previously, the embedded microcomputer 222 displays 902 the previously stored patient information on the patient information screen. The embedded microcomputer 222 prompts 903 a user to enter a name of a patient. The embedded microcomputer 222 receives the entered name of the patient and determines 915 an availability of a patient identifier. If the patient identifier is not available, the embedded microcomputer 222 prompts 916 the user to enter the patient identifier and proceeds to step 918. If the patient identifier is available, the embedded microcomputer 222 disallows 917 entry of the patient identifier by the user. The embedded microcomputer 222 prompts 918 the user to enter a name of a surgeon performing the surgery. The embedded microcomputer 222 prompts 919 the user to enter surgery type. The embedded microcomputer 222 prompts 920 the user to enter surgery details. The embedded microcomputer 222 determines 921 whether a show patient information checkbox is checked on the patient information screen. If the show patient information checkbox is checked on the patient information screen, the embedded microcomputer 222 displays 923 the patient information on the run screen. If the show patient information checkbox is not checked on the patient information screen, the embedded microcomputer 222 does not display 922 the patient information on the run screen. If the patient information was not entered previously, the embedded microcomputer 222 displays 904 the default patient information and prompts 903 the user to enter the name of the patient and continues with steps 915 to 923 disclosed above.

The embedded microcomputer 222 determines 905 whether the exit button is clicked on the patient information screen. If the exit button is clicked on the patient information screen, the embedded microcomputer 222 determines 906 whether the patient information is modified. If the patient information is not modified, the embedded microcomputer 222 exits 907 to the run screen. If the patient information is modified, the embedded microcomputer 222 prompts 908 the user to save the modified patient information. The embedded microcomputer 222 determines 909 whether the save and exit button is clicked on the patient information screen. If the save and exit button is clicked on the patient information screen, the embedded microcomputer 222 saves 910 the modified patient information and exits to the run screen. The embedded microcomputer 222 determines 911 whether the exit without save button is clicked on the patient information screen. If the exit without save button is clicked on the patient information screen, the embedded microcomputer 222 discards 912 the modified patient information and exits to the run screen. The embedded microcomputer 222 determines 913 whether the complete surgery button is clicked on the patient information screen. If the complete surgery button is clicked on the patient information screen, the embedded microcomputer 222 clears 914 the patient information and loads the default patient information.

Figure 10:
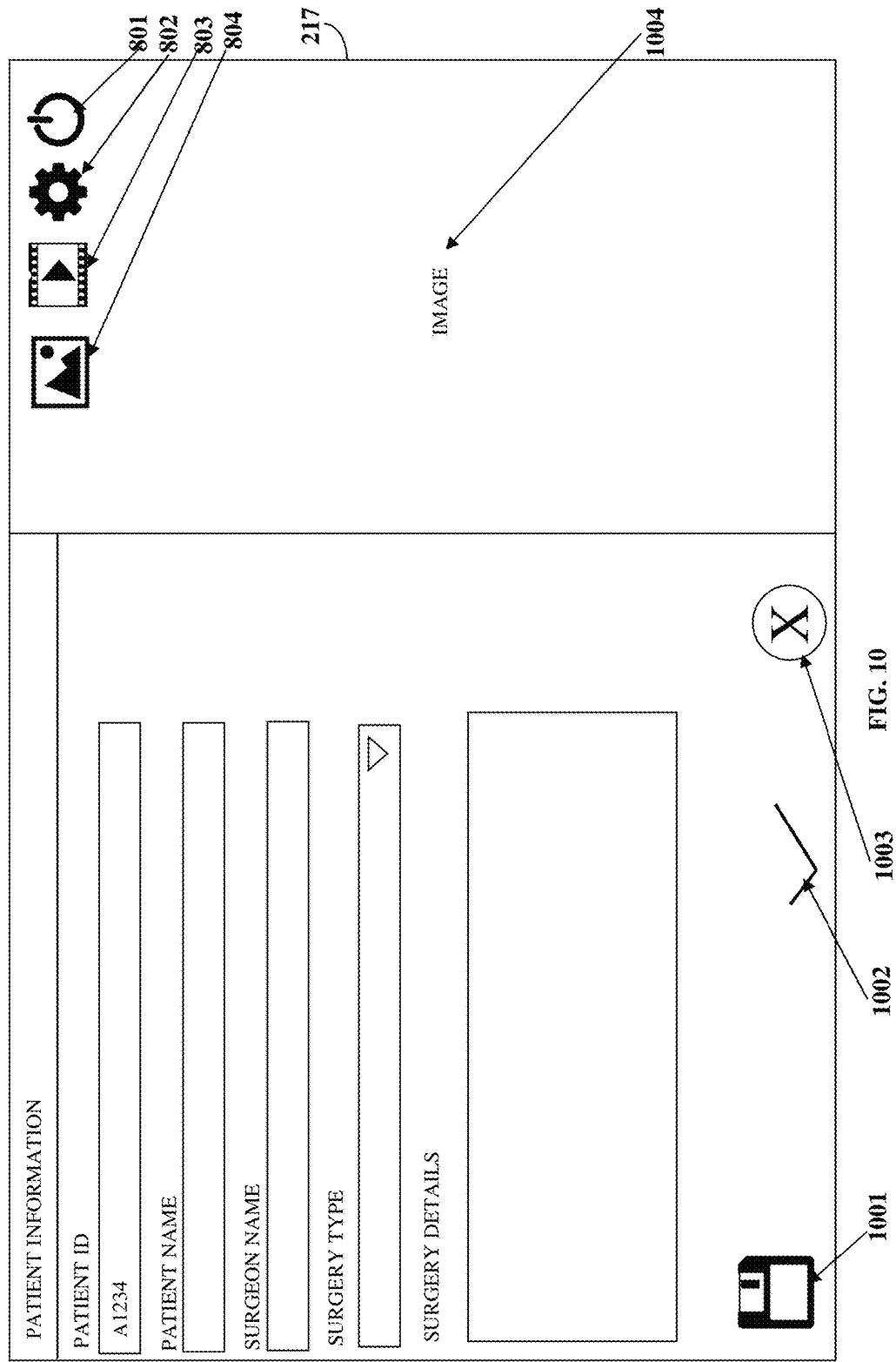
FIG. 10 exemplarily illustrates a screenshot of the tactile user interface of the display unit, displaying the patient information screen for entering patient information to be associated with images of a surgical site.

FIG. 10 exemplarily illustrates a screenshot of the tactile user interface 217 of the display unit 216 exemplarily illustrated in FIG. 2, displaying the patient information screen for entering patient information to be associated with images of a surgical site. The tactile user interface 217 displays buttons, for example, a power off button 801, a camera settings button 802, a video record button 803, and an image snap button 804. The patient information screen displays text boxes for receiving patient information comprising, for example, patient identifier (ID), patient name, surgeon name, and surgery details, and a dropdown menu for providing options to select a type of surgery. The embedded microcomputer 222 of the display unit 216 exemplarily illustrated in FIG. 3, prompts a user to enter the patient information as disclosed in the detailed description of FIGS. 9A-9B. The user enters the patient ID, the patient name, the surgeon name, and surgery details in the corresponding text boxes and selects the surgery type from the list of options provided in the corresponding dropdown menu. The patient information screen displays a save button 1001, a complete surgery button 1002, and an exit button 1003 as exemplarily illustrated in FIG. 10, for performing respective functions as disclosed in the detailed description of FIGS. 9A-9B. The tactile user interface 217 displays a live image 1004 adjacent to the patient information screen as exemplarily illustrated in FIG. 10. When the live image 1004 is displayed on the tactile user interface 217 with up to a 4K UHD resolution, the user may click on the image snap button 804 to capture an image of a surgical site being streamed or click on the video record button 803 to record a video of the surgical site being streamed. In an embodiment, the user can enter the patient information while viewing the live image 1004. The embedded microcomputer 222 overlays the patient information on the live image 1004 for visualization by the user. The user may view the patient information along with the live image 1004 on the tactile user interface 217 while performing a surgery. The user may click on the power off button 801 to power off the surgical visualization and recording system 200 exemplarily illustrated in FIGS. 2-3.

Figure 11A:
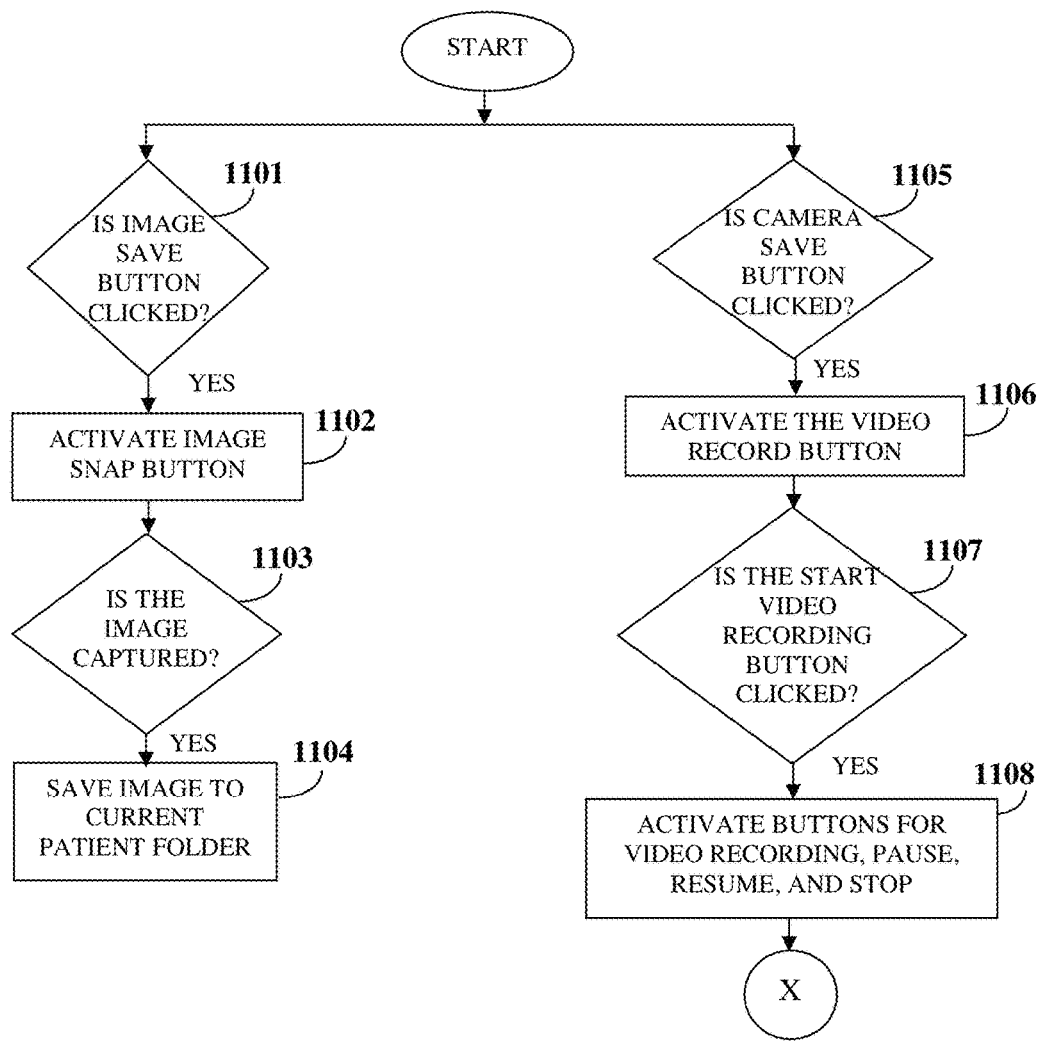
FIGS. 11A-11B exemplarily illustrate a flowchart comprising the steps performed by the embedded microcomputer of the display unit based on user inputs received on a video recording and image capture screen rendered on the tactile user interface of the display unit.
Figure 11B:
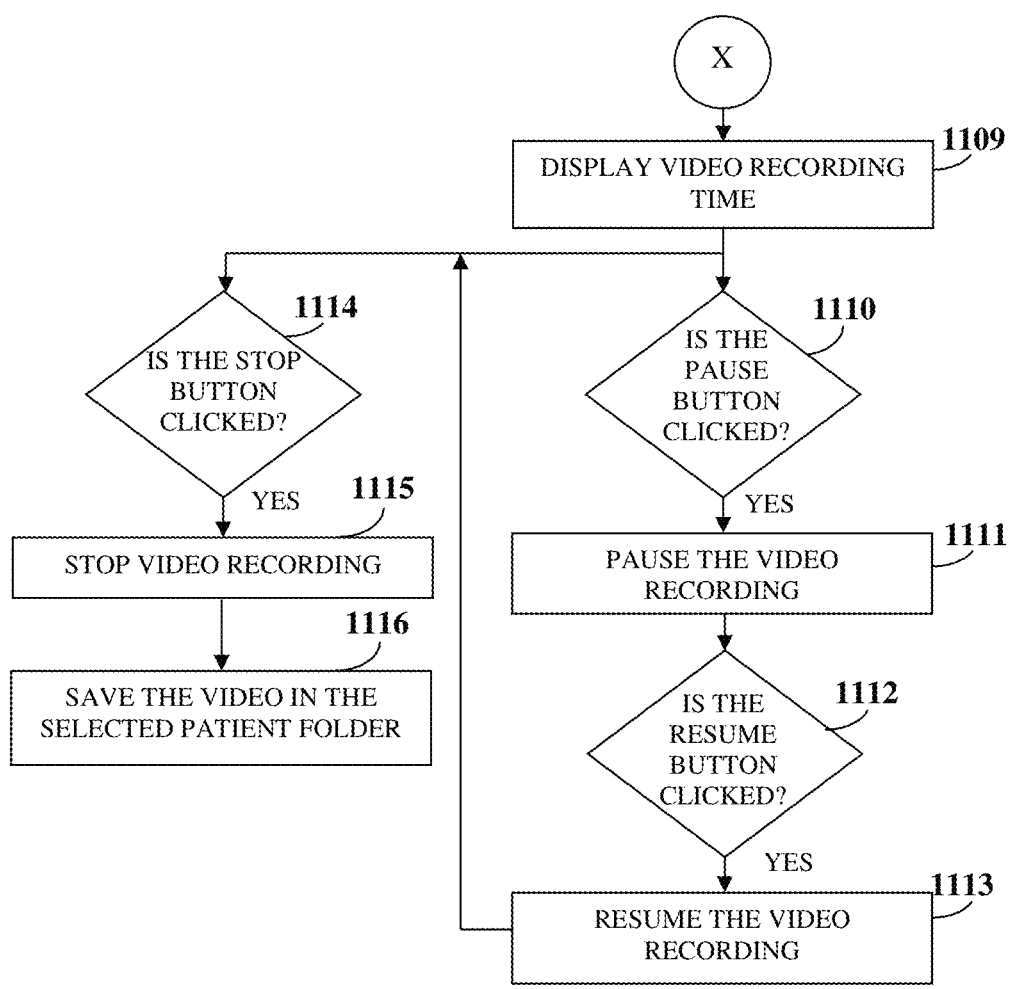

FIGS. 11A-11B exemplarily illustrate a flowchart comprising the steps performed by the embedded microcomputer 222 of the display unit 216 exemplarily illustrated in FIG. 3, based on user inputs received on a video recording and image capture screen rendered on the tactile user interface 217 of the display unit 216 exemplarily illustrated in FIG. 2. The video recording and image capture screen comprises, for example, an image save button, a camera save button, an image snap button, a video record button, a pause button, a resume button, and a stop button. A user must select the patient identifier beforehand for the embedded microcomputer 222 to render the video recording and image capture screen on the display unit 216. The embedded microcomputer 222 determines 1101 whether the image save button is clicked on the video recording and image capture screen. If the image save button is clicked on the video recording and image capture screen, the embedded microcomputer 222 activates 1102 the image snap button on the video recording and image capture screen. The embedded microcomputer 222 determines whether the image snap button is clicked and determines 1103 whether the image sensor 220 of the ultrahigh definition (UHD) camera system 201 exemplarily illustrated in FIG. 3, captured an image. If the image is captured, the embedded microcomputer 222 saves 1104 the captured image to a current patient folder in the storage device 234 and/or the removable drive 218 exemplarily illustrated in the FIG. 3.

The embedded microcomputer 222 determines 1105 whether the camera save button is clicked on the video recording and image capture screen. If the camera save button is clicked on the video recording and image capture screen, the embedded microcomputer 222 activates 1106 the video record button. The embedded microcomputer 222 determines 1107 whether the video record button is clicked on the video recording and image capture screen. If the video record button is clicked on the video recording and image capture screen, the embedded microcomputer 222 activates 1108 buttons for video recording, pause, resume, and stop on the video recording and image capture screen. The embedded microcomputer 222 displays 1109 video recording time on the video recording and image capture screen. The embedded microcomputer 222 determines 1110 whether the pause button is clicked on the video recording and image capture screen. If the pause button is clicked on the video recording and image capture screen, the embedded microcomputer 222 pauses 1111 the video recording. The embedded microcomputer 222 determines 1112 whether the resume button is clicked on the video recording and image capture screen. If the resume button is clicked on the video recording and image capture screen, the embedded microcomputer 222 resumes 1113 the video recording. The embedded microcomputer 222 determines 1114 whether the stop button is clicked on the video recording and image capture screen. If the stop button is clicked on the video recording and image capture screen, the embedded microcomputer 222 stops 1115 recording the video. The embedded microcomputer 222 saves 1116 the recorded video in the selected patient folder in the storage device 234 and/or the removable drive 218.

Figure 12:
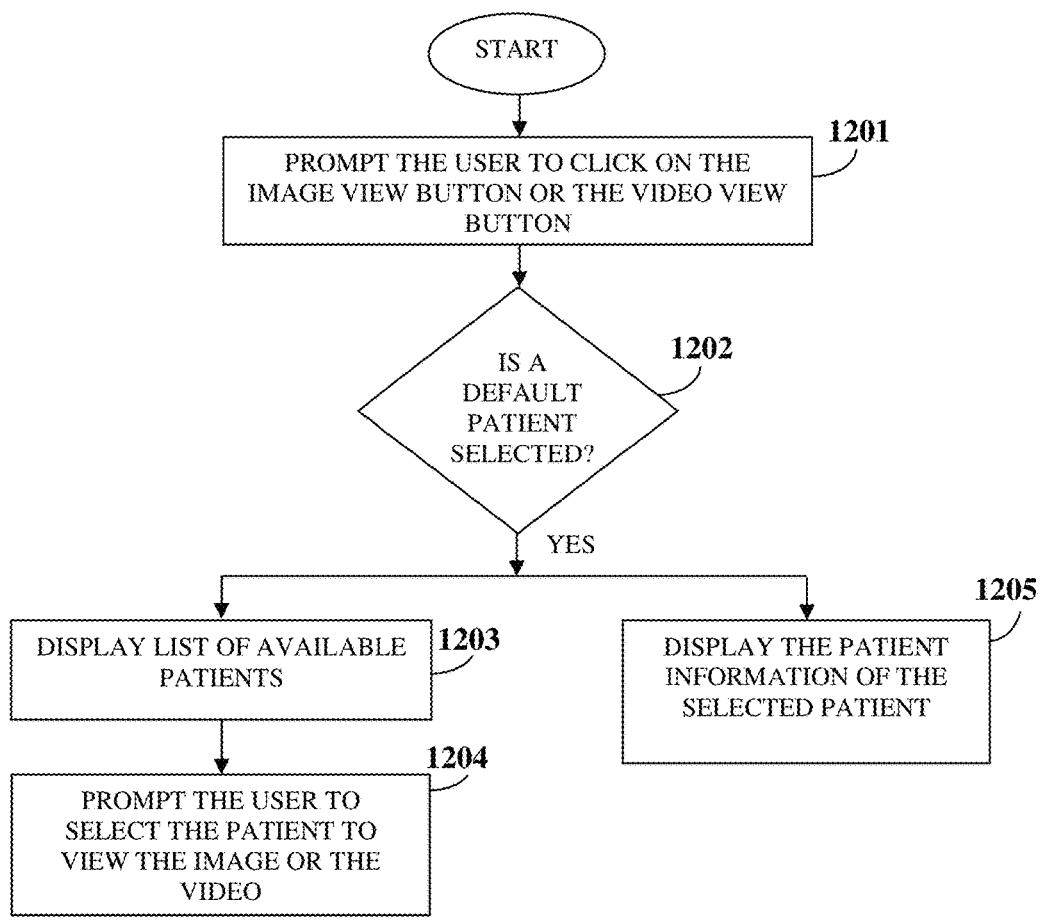
FIG. 12 exemplarily illustrates a flowchart comprising the steps performed by the embedded microcomputer of the display unit based on user inputs received on a media viewer screen rendered on the tactile user interface of the display unit.

FIG. 12 exemplarily illustrates a flowchart comprising the steps performed by the embedded microcomputer 222 of the display unit 216 exemplarily illustrated in FIG. 3, based on user inputs received on a media viewer screen rendered on the tactile user interface 217 of the display unit 216 exemplarily illustrated in FIG. 2. The embedded microcomputer 222 prompts 1201 a user to click on the image view button or the video view button disclosed in the detailed description of FIGS. 6A-6B. If the image view button or the video view button is clicked, the embedded microcomputer 222 determines 1202 whether a default patient is selected. If the default patient is selected, the embedded microcomputer 222 displays 1203 a list of available patients on the media viewer screen. The embedded microcomputer 222 prompts 1204 the user to select a patient for viewing a corresponding image or video. The embedded microcomputer 222 receives a selection of the patient to view the image or the video. The embedded microcomputer 222 displays 1205 the patient information based on the received selection of the patient on the media viewer screen. The embedded microcomputer 222 does not permit the user to view an image or a video that does not correspond to a selected patient.

It will be readily apparent in different embodiments that the various methods, algorithms, and computer programs disclosed herein are implemented on non-transitory computer readable storage media appropriately programmed for computing devices. The non-transitory computer readable storage media participate in providing data, for example, instructions that are read by a computer, a processor or a similar device. In different embodiments, the "non-transitory computer readable storage media" also refer to a single medium or multiple media, for example, a centralized database, a distributed database, and/or associated caches and servers that store one or more sets of instructions that are read by a computer, a processor or a similar device. The "non-transitory computer readable storage media" also refer to any medium capable of storing or encoding a set of instructions for execution by a computer, a processor or a similar device and that causes a computer, a processor or a similar device to perform any one or more of the methods disclosed herein. Common forms of the non-transitory computer readable storage media comprise, for example, a floppy disk, a flexible disk, a hard disk, magnetic tape, a laser disc, a Blu-ray Disc® of the Blu-ray Disc Association, any magnetic medium, a compact disc-read only memory (CD-ROM), a digital versatile disc (DVD), any optical medium, a flash memory card, punch cards, paper tape, any other physical medium with patterns of holes, a random access memory (RAM), a programmable read only memory (PROM), an erasable programmable read only memory (EPROM), an electrically erasable programmable read only memory (EEPROM), a flash memory, any other memory chip or cartridge, or any other medium from which a computer can read.

In an embodiment, the computer programs that implement the methods and algorithms disclosed herein are stored and transmitted using a variety of media, for example, the computer readable media in several manners. In an embodiment, hard-wired circuitry or custom hardware is used in place of, or in combination with, software instructions for implementing the processes of various embodiments. Therefore, the embodiments are not limited to any specific combination of hardware and software. The computer program codes comprising computer executable instructions can be implemented in any programming language. Examples of programming languages that can be used comprise C, C++, C#, Java®, JavaScript®, Fortran, Ruby, Perl®, Python®, Visual Basic®, hypertext preprocessor (PHP), Microsoft® .NET, Objective-C®, etc. Other object-oriented, functional, scripting, and/or logical programming languages can also be used. In an embodiment, the computer program codes or software programs are stored on or in one or more mediums as object code. In another embodiment, various aspects of the method and the surgical visualization and recording system (SVRS) 200 exemplarily illustrated in FIGS. 2-3, disclosed herein are implemented in a non-programmed environment comprising documents created, for example, in a hypertext markup language (HTML), an extensible markup language (XML), or other format that render aspects of a graphical user interface (GUI) or perform other functions, when viewed in a visual area or a window of a browser program. In another embodiment, various aspects of the method and the SVRS 200 disclosed herein are implemented as programmed elements, or non-programmed elements, or any suitable combination thereof.

Where databases are described such as the internal database 238 and the external database 304 in the external system 303 exemplarily illustrated in FIG. 3, it will be understood by one of ordinary skill in the art that (i) alternative database structures to those described may be employed, and (ii) other memory structures besides databases may be employed. Any illustrations or descriptions of any sample databases disclosed herein are illustrative arrangements for stored representations of information. In an embodiment, any number of other arrangements are employed besides those suggested by tables illustrated in the drawings or elsewhere. Similarly, any illustrated entries of the databases represent exemplary information only; one of ordinary skill in the art will understand that the number and content of the entries can be different from those disclosed herein. In another embodiment, despite any depiction of the databases as tables, other formats including relational databases, object-based models, and/or distributed databases are used to store and manipulate the data types disclosed herein. Object methods or behaviors of a database can be used to implement various processes such as those disclosed herein. In another embodiment, the databases are, in a known manner, stored locally or remotely from a device that accesses data in such a database. In embodiments where there are multiple databases in the surgical visualization and recording system 200, the databases are integrated to communicate with each other for enabling simultaneous updates of data linked across the databases, when there are any updates to the data in one of the databases.

The method and the surgical visualization and recording system (SVRS) 200 disclosed herein can be configured to work in a network environment comprising one or more computers that are in communication with one or more devices via the network 301 exemplarily illustrated in FIG. 3. In an embodiment, the computers communicate with the devices directly or indirectly, via a wired medium or a wireless medium such as the Internet, a local area network (LAN), a wide area network (WAN) or the Ethernet, a token ring, or via any appropriate communications mediums or combination of communications mediums. Each of the devices comprises processors, examples of which are disclosed above, that are adapted to communicate with the computers. In an embodiment, each of the computers is equipped with a network communication device, for example, a network interface card, a modem, or other network connection device suitable for connecting to the network 301. Each of the computers and the devices executes an operating system, examples of which are disclosed above. While the operating system may differ depending on the type of computer, the operating system provides the appropriate communications protocols to establish communication links with the network 301. Any number and type of machines may be in communication with the computers.

The method and the surgical visualization and recording system (SVRS) 200 disclosed herein are not limited to a particular computer system platform, microprocessor, operating system, or network. In an embodiment, one or more aspects of the method and SVRS 200 disclosed herein are distributed among one or more computer systems, for example, servers configured to provide one or more services to one or more client computers, or to perform a complete task in a distributed system. For example, one or more aspects of the method and the SVRS 200 disclosed herein are performed on a client-server system that comprises components distributed among one or more server systems that perform multiple functions according to various embodiments. These components comprise, for example, executable, intermediate, or interpreted code, which communicate over the network 301 using a communication protocol. The method and the SVRS 200 disclosed herein are not limited to be executable on any particular system or group of systems, and are not limited to any particular distributed architecture, network, or communication protocol.

The foregoing examples have been provided merely for explanation and are in no way to be construed as limiting of the method and the surgical visualization and recording system (SVRS) 200 disclosed herein. While the method and the SVRS 200 have been described with reference to various embodiments, it is understood that the words, which have been used herein, are words of description and illustration, rather than words of limitation. Furthermore, although the method and the SVRS 200 have been described herein with reference to particular means, materials, and embodiments, the method and SVRS 200 are not intended to be limited to the particulars disclosed herein; rather, the method and the SVRS 200 extend to all functionally equivalent structures, methods and uses, such as are within the scope of the appended claims. While multiple embodiments are disclosed, it will be understood by those skilled in the art, having the benefit of the teachings of this specification, that the method and the SVRS 200 disclosed herein are capable of modifications and other embodiments may be effected and changes may be made thereto, without departing from the scope and spirit of the method and the SVRS 200 disclosed herein.

I claim:

1. A method for capturing, communicating, and displaying images of a surgical site with up to an ultrahigh definition resolution in association with patient information in real time during a surgery, said method comprising:
   providing a surgical visualization and recording system comprising:
   an ultrahigh definition camera system comprising an optical component and an image sensor positioned at a proximal end of a surgical scope device, said image sensor in optical communication with said optical component for receiving reflected light from said surgical site via said optical component and capturing images of said surgical site with up to said ultrahigh definition resolution;
   a display unit comprising an embedded microcomputer in operable communication with said ultrahigh definition camera system, said embedded microcomputer comprising at least one processor configured to execute computer program instructions for receiving, transforming, and processing said captured images of said surgical site; and
   said display unit further comprising a tactile user interface in operable communication with said embedded microcomputer for receiving one or more user inputs for controlling operation of said ultrahigh definition camera system and for displaying said captured images of said surgical site with up to said ultrahigh definition resolution;
   receiving said patient information via said tactile user interface of said display unit of said surgical visualization and recording system by said embedded microcomputer of said display unit;
   capturing and communicating said images of said surgical site with up to said ultrahigh definition resolution by said image sensor of said ultrahigh definition camera system of said surgical visualization and recording system to said embedded microcomputer of said display unit in said real time, on receiving one or more user inputs via one of said tactile user interface of said display unit and one or more input devices operably connected to said embedded microcomputer of said display unit;
   associating said captured and communicated images of said surgical site with said received patient information by said embedded microcomputer of said display unit in said real time; and
   displaying said captured and communicated images of said surgical site associated with said received patient information with up to said ultrahigh definition resolution by said tactile user interface of said display unit in said real time.

2. The method of claim 1, further comprising recording said captured and communicated images of said surgical site with up to said ultrahigh definition resolution and with said received patient information in a storage device by said embedded microcomputer of said display unit in said real time.

3. The method of claim 1, further comprising securely storing said captured and communicated images of said surgical site with said received patient information on an external system directly in said real time by said embedded microcomputer of said display unit.

4. The method of claim 1, further comprising storing said captured and communicated images of said surgical site with said received patient information in a cloud computing environment over a network in said real time by said embedded microcomputer of said display unit.

5. The method of claim 1, further comprising controlling said capture, recording, and said display of said images of said surgical site with up to said ultrahigh definition resolution by said embedded microcomputer of said display unit, on receiving said one or more user inputs via said one of said tactile user interface of said display unit and said one or more input devices.

6. The method of claim 1, further comprising transmitting said captured and communicated images of said surgical site with up to said ultrahigh definition resolution and with said received patient information in said real time by said embedded microcomputer of said display unit to a client application on a user device via a network for allowing viewing of said captured and communicated images of said surgical site with said received patient information on said user device in said real time.

7. The method of claim 1, further comprising organizing said captured and communicated images of said surgical site with said received patient information in a file system by said embedded microcomputer of said display unit.

8. The method of claim 1, wherein said patient information comprises a patient identifier, a patient name, a surgeon name, a type of said surgery, a description of said surgery, and a date of said surgery.

9. The method of claim 1, further comprising controlling one or more of a plurality of camera parameters of said ultrahigh definition camera system by said embedded microcomputer of said display unit, on receiving said one or more user inputs via said one of said tactile user interface of said display unit and said one or more input devices, and wherein said camera parameters comprise white balance, brightness, sharpness, contrast, gamma, saturation, resolution, gain, exposure, and frame rate.

10. The method of claim 1, wherein said one or more input devices comprise a foot switch and a portable wireless controller operably connected to said embedded microcomputer of said display unit.

11. The method of claim 1, wherein said ultrahigh definition resolution is a resolution of 3840 pixels×2160 lines.

12. A surgical visualization and recording system for capturing, communicating, and displaying images of a surgical site with up to an ultrahigh definition resolution in association with patient information in real time during a surgery, said surgical visualization and recording system comprising:
an ultrahigh definition camera system comprising:
an optical component positioned at a proximal end of a surgical scope device; and
an image sensor in optical communication with said optical component for receiving reflected light from said surgical site via said optical component and capturing and communicating said images of said surgical site with up to said ultrahigh definition resolution to an embedded microcomputer of a display unit in said real time, on receiving one or more user inputs via one of said tactile user interface of said display unit and one or more input devices operably connected to said embedded microcomputer of said display unit; and
said display unit in operable communication with said ultrahigh definition camera system, said display unit comprising:
a tactile user interface for receiving one or more user inputs for controlling operation of said ultrahigh definition camera system and for displaying said captured and communicated images of said surgical site with up to said ultrahigh definition resolution; and
said embedded microcomputer in operable communication with said tactile user interface, said embedded microcomputer comprising at least one processor configured to execute computer program instructions defined by modules of said embedded microcomputer for receiving, transforming, and processing said captured and communicated images of said surgical site, said modules of said embedded microcomputer comprising:
a data communication module for receiving said patient information via said tactile user interface and said one or more user inputs for controlling said operation of said ultrahigh definition camera system via said one of said tactile user interface and said one or more input devices;
said data communication module for receiving said captured and communicated images of said surgical site with up to said ultrahigh definition resolution from said image sensor of said ultrahigh definition camera system in said real time;
a patient information association module for associating said captured and communicated images of said surgical site with said received patient information in said real time; and
a display module for displaying said captured and communicated images of said surgical site associated with said received patient information with up to said ultrahigh definition resolution on said tactile user interface in said real time.

13. The surgical visualization and recording system of claim 12, wherein said modules of said embedded microcomputer of said display unit further comprise an image recorder for recording said captured and communicated images of said surgical site with up to said ultrahigh definition resolution and with said received patient information in a storage device in said real time.

14. The surgical visualization and recording system of claim 12, wherein said modules of said embedded microcomputer of said display unit further comprise a storage module for securely storing said captured and communicated images of said surgical site with said received patient information on an external system directly in said real time.

15. The surgical visualization and recording system of claim 12, wherein said modules of said embedded microcomputer of said display unit further comprise a storage module for storing said captured and communicated images of said surgical site with said received patient information in a cloud computing environment over a network in said real time.

16. The surgical visualization and recording system of claim 12, wherein said modules of said embedded microcomputer of said display unit further comprise a control module for controlling said capture, recording, and said display of said images of said surgical site with up to said ultrahigh definition resolution, on receiving said one or more user inputs via said one of said tactile user interface of said display unit and said one or more input devices.

17. The surgical visualization and recording system of claim 12, wherein said data communication module of said embedded microcomputer of said display unit transmits said captured and communicated images of said surgical site with up to said ultrahigh definition resolution and with said received patient information in said real time to a client application on a user device via a network for allowing viewing of said captured and communicated images of said surgical site with said received patient information on said user device in said real time.

18. The surgical visualization and recording system of claim 12, wherein said patient information association module of said embedded microcomputer of said display unit organizes said captured and communicated images of said surgical site with said received patient information in a file system.

19. The surgical visualization and recording system of claim 12, wherein said ultrahigh definition camera system further comprises a universal serial bus interface for allowing streaming of said captured images with up to said ultrahigh definition resolution in an ultrahigh definition digital display format from said image sensor of said ultrahigh definition camera system to one or more of said display unit, an external system, and a cloud computing environment in said real time.

20. The surgical visualization and recording system of claim 12, wherein said modules of said embedded microcomputer of said display unit further comprise a control module for controlling one or more of a plurality of camera parameters of said ultrahigh definition camera system, on receiving said one or more user inputs via said one of said tactile user interface of said display unit and said one or more input devices, and wherein said camera parameters comprise white balance, brightness, sharpness, contrast, gamma, saturation, resolution, gain, exposure, and frame rate.

21. The surgical visualization and recording system of claim 12, wherein said one or more input devices comprise a foot switch and a portable wireless controller operably connected to said embedded microcomputer of said display unit.

22. The surgical visualization and recording system of claim 12, wherein said ultrahigh definition camera system further comprises a C-mount interface operably coupled to said optical component of said ultrahigh definition camera system for adjusting a focal length of said optical component from about 18 millimeters to about 35 millimeters.

23. The surgical visualization and recording system of claim 12, wherein said ultrahigh definition camera system is waterproof.

* * * * *